US006323331B1

(12) United States Patent
Levine

(10) Patent No.: US 6,323,331 B1
(45) Date of Patent: *Nov. 27, 2001

(54) BECLIN-RELATED NUCLEIC ACID MOLECULES, AND USES THEREOF

(75) Inventor: Beth C. Levine, Scarborough, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,667

(22) PCT Filed: Sep. 12, 1997

(86) PCT No.: PCT/US97/16358

§ 371 Date: Jul. 16, 1999

§ 102(e) Date: Jul. 16, 1999

(87) PCT Pub. No.: WO98/11256

PCT Pub. Date: Mar. 19, 1998

Related U.S. Application Data

(63) Continuation-in-part of application No. 08/712,939, filed on Sep. 13, 1996, now Pat. No. 5,858,669.

(51) Int. Cl.$^7$ .......................... C07H 21/04; C07K 14/00; C12Q 1/68

(52) U.S. Cl. .................... 536/23.1; 536/24.33; 536/23.5; 536/24.31; 530/350; 435/6

(58) Field of Search ............................... 435/6; 536/23.1, 536/24.31, 24.33, 23.5; 530/350

(56) References Cited

U.S. PATENT DOCUMENTS 4,742,003 * 5/1988 Derynck et al. .................. 435/68
5,858,669 * 1/1999 Levine ............................. 435/6

OTHER PUBLICATIONS

Genbank Accession No. L38932, Oct. 1995.*
Genbank Accession No. U17999, May 1995.*
Clontech Catalog, pp. 71 and 79, 1995–1996.*
Aita, V.M., et al. (1999) "Cloning and Genomic Organization of Beclin 1, a Candidate Tumor Suppressor Gene on Chromosome 17q21", *Genomics*, 59:59–65. (Exhibit 2).
Gordon, G.W., et al., (1998) "Quantitative Fluorescence Resonance Energy Transfer Measurements Using Fluorescence Microscopy", *Biophysical Journal*, 74:2702–2713 (Exhibit 3).
Liang, X.H., et al., (1999) "Induction of Autophagy and Inhibition of Tumorigenesis by Beclin 1", *Nature*, 402:672–676. (Exhibit 4).
Liang, X.H., et al., (1998) "Protection against Fatal Sindbis Virus Encephalitis by Beclin, a Novel Bcl–2–Interacting Protein", *Journal of Virology*, 72(1):8586–8596. (Exhibit 5).

Cropp, C.S., et al. (1993) "Identification of Three Regions on Chromosome 17q in Primary Human Breast Carcinomas Which Are Frequently Deleted" 53:5617–5619 (Exhibit 1).
Eccles, D.M., et al. (1992) "Early loss heterozygosity on 17q in ovarian cancer." *Oncogene* 7:2069–2072, (Exhibit 2).
Friedman, L.S., et al. (1995) "Twenty–two genes from chromosome 17q21: cloning, sequencing and characterization of mutations in breast cancer families and tumors." *Genomics* 25:256–263, (Exhibit 3).
Futreal, P.A., et al. (1994) "BRCA1 mutations in primary breast and ovarian carcinomas." *Science* 266:120–122, (Exhibit 4).
Futreal, P.A., et al. (1992) "Detection of frequent allelic loss on proximal chromosome 17q in sporadic breast carcinoma using microsatellite length. polymorphisms" *CancerRes* 52:2624–2627, (Exhibit 5).
Hosking, L., et al. (1995) "A somatic BRCA1 mutation in an ovarian tumour." *Nature Genet* 9:343–344, (Exhibit 6).
Levine, B., et al. (1993) "Conversion of lytic to persistant alphavirus infection by the bcl–2 cellular oncogene" *Nature*, 361:739–742 (Exhibit 7).
Merajver, S.D., et al. (1995) "Somatic mutations in the BRCA1 gene in sporadic ovarian tumours." *Nature Genet*. 9:439–443, (Exhibit 8).
Rommens, J. M., et al. (1995) "Generation of the transcription map at the HSD17B locus centromeric to BRCA1 at 17q21." *Genomics* 28:530–542, (Exhibit 9).
Saito, H., et al. (1993) "Detailed deletion mapping of chromosome 17q in ovarian and breast cancers: 2–cM region on 17q21.3 often and commonly deleted in tumors." *Cancer Res.* 53:3382–3385, (Exhibit 10).

(List continued on next page.)

Primary Examiner—W. Gary Jones
Assistant Examiner—Jeanine Goldberg
(74) Attorney, Agent, or Firm—John P. White; Cooper & Dunham LLP

(57) ABSTRACT

This invention provides for an isolated nucleic acid which encodes a wildtype human Beclin and a mutant human Beclin. This invention also provides a vector containing the isolated nucleic acid which encodes a wildtype human Beclin. This invention also provides for a method of producing a wildtype human Beclin. This invention also provides for a purified, wildtype human Beclin. This invention also provides for a method for determining whether a subject has a predisposition for cancer. This invention also provides a method for determining whether a subject has cancer. This invention also provides for a method for inhibiting cell proliferation in cells unable to regulate themselves. This invention also provides for a method for treating a subject who has cancer. This invention also provides for a pharmaceutical composition composed of the and a pharmaceutically acceptable carrier. This invention also provides a pharmaceutical composition composed of the wildtype human Beclin. This invention also provides a method for detecting a mutant human Beclin in a subject. This invention also provides a method for treating a subject unable to control apoptosis in the cells of the subject.

19 Claims, 25 Drawing Sheets

OTHER PUBLICATIONS

Sato, T., et al. (1994) "Interactions among members of the Bcl–2 protein family analyzed with a yeast two–hybrid system." *Proc. Natl. Acad. Sci USA* 91:9238–9242, (Exhibit 11).

Takhashi, H., et al. (1995) "Mutation analysis of the BRCA1 gene in ovarian cancers." *Cancer Res.* 55:2998–3002, (Exhibit 12).

Tangir, J., et al. (1996) "A 400 kb novel deletion unit centromeric to the BRCA1 in sporadic epitheliel ovarian cancer." *Oncogene* 12:735–740, (Exhibit 13); and.

Yan–Feng, et al. (1993) "Allelic loss in ovarian cancer." *Int.J.Cancer* 54:546–551, (Exhibit 14).

* cited by examiner

FIGURE 1A

```
  1  MEGSKTSNNSTMQVSFVCQRCSQPLKLDTS
 31  FKILDRVTIQELTAPLLTTAQAKPGETQEE
 61  ETNSGEEPFIETPRQDGVSRRFIPPARMMS
 91  TESANSFTLIGEVSDGGTMENLSRRLKVTG
121  DLFDIMSGQTDVDHPLCEECTDTLLDQLDT
151  QLNVTENECQNYKRCLEILEQMNEDDSEQL
181  QMELKELVQAEERLDQEEAQYREYSEFKRQ
211  NRKIVAERLDQEEAQYREYSEFKRQNVFHS
241  LEDDELKSVENQMRYAQTQLDKLKKTNVF
271  NATFHIWHSGQFGTINNFRLGRLPSVPVEW
301  NEINAAWGQTVLLHALANKMGLKFQRYRL
331  VPYGNHSYLESLTDKSKELPLYCSGGLRFF
361  WDNKFDHAMVAFLDCVQQFKEEVEKGETRF
391  CLPYRMDVEKGKIEDTGGSGGSYSIKTQFN
421  SEEQWTKALKFMLTNLKWGLAWVSSQFYNK
```

FIGURE 1B

```
1/1                                                                                                                          31/11                                                           61/21
ATG GAA GGG TCT AAG ACG TCC AAC AAC AGC ACC ATG CAG GTG AGC TTC GTG TGC CAG CGC TGC AGC CAG CCC CTG AAA CTG GAC ACG AGT
 M   E   G   S   K   T   S   N   N   S   T   M   Q   V   S   F   V   C   Q   R   C   S   Q   P   L   K   L   D   T   S
91/31                                                                                                        121/41                                                          151/51
TTC AAG ATC CTG GAC CGT GTC ACC ATC CAG GAA CTC ACA GCT CCA TTA CTT ACC ACA GCC AAA CCA GGA GAG ACC CAG GAG GAA
 F   K   I   L   D   R   V   T   I   Q   E   L   T   A   P   L   L   T   T   A   Q   A   K   P   G   E   T   Q   E   E
181/61                                                                                                       211/71                                                           241/81
GAG ACT AAC TCA GGA GAG GAG CCA TTT ATT GAA ACT CCT CGC CAG GAT GGT GTC TCT CGC AGA TTC ATC CCC AGA TTC ATC CCA GCC AGG ATG ATG TCC
 E   T   N   S   G   E   E   P   F   I   E   T   P   R   Q   D   G   V   S   R   R   F   I   P   P   A   R   M   M   S
271/91                                                                                                       301/101                                                          331/111
ACA GAA AGT GCC AAC AGC TTC ACT CTG ATT GGG GAG GTA TCT GAT GGC GGC ACC ATG GAG AAC CTC AGC AGA AGA CTG AAG GTC ACT GGG
 T   E   S   A   N   S   F   T   L   I   G   E   V   S   D   G   G   T   M   E   N   L   S   R   R   L   K   V   T   G
361/121                                                                                                      391/131                                                          421/141
GAC CTT TTT GAC ATC ATG TCG GGC CAG ACA GAT GTG GAT CAC CCA CTC TGT GAG GAA ATC TAC ACA GAT ACT CTT TTA GAC CAG CTG GAC ATT
 D   L   F   D   I   M   S   G   Q   T   D   V   D   H   P   L   C   E   E   I   Y   T   D   T   L   L   D   Q   L   D
451/151                                                                                                      481/161                                                          511/171
CAG CTC AAC GTC ACT GAA AAT GAG TGT CAG AAC TAC AAA CGC CTC GAG ATC TTA CTG GAA ATG GAA AAG AAG AAC ATG CGC AAG ATA GTG GTA GAA
 Q   L   N   V   T   E   N   E   C   Q   N   Y   K   R   L   E   I   L   L   E   M   E   K   N   M   R   K   I   V   E
541/181                                                                                                      571/191                                                          601/201
CAG ATG GAG CTA AAG GAG GAG CTA GCA CTA GAG GAG GAG GAG AGG CTG ATC CAG GAG GAG GAC GTG GAA TAC AGT AAG GAG TAC AGC GAA
 Q   M   E   L   K   E   E   L   A   L   E   E   E   E   R   L   I   Q   E   E   D   V   E   K   N   R   E   Y   S   E
631/211                                                                                                      661/221                                                          691/231
AAT CTC GAG AAG GTC CAG GCT GAG GCT GAG AGT GTT GGA AAC ATC GAT CAG GAG GAA GCT CAG TAT CAG CAG ACG CAG ACG CAG CTG CCC AGT GTT CAG CAG TAC TTT CAG TTT
 N   L   E   K   V   Q   A   E   A   E   S   V   E   N   Q   M   R   Y   A   N   N   F   R   L   G   R   L   P   S   V   F
721/241                                                                                                      751/251                                                          781/261
CTG GAG CTG GAT GAT GAA CTC CAC AGT TGG CAG CAG ACT CTG GAG CTG TTG CTC CTG CTC ATC CAT GCA AAA ATG TCT AAG GAG CTG CCG TTA TAC TGT TCT GGG GAG ACA CCC CGG TTC TGG
 L   E   L   D   D   E   L   H   S   W   Q   Q   T   L   E   L   L   L   L   I   H   A   L   A   N   K   M   G   L   Y   C   S   V   P   V   E   W
811/271                                                                                                      841/281                                                          871/291
AAT GCA ACC TTC AAT GCT GCT TGG CAC AGT GGA CAG TTT GGC ACA ATC ACA ATT AAC AAC TTC CAT GCT AAG AGG CTG GGT CGC CTG CCC AGT GTT CAG CAG TAC TTT CAG TTT
 N   A   T   F   N   A   A   W   H   S   G   Q   F   G   T   I   N   N   F   F   R   L   G   R   L   P   S   V   Q   Q   Y   F   Q   F
901/301                                                                                                      931/311                                                          961/321
AAT GAG ATT AAT GCT GCT TGG CAC AGT GGA CAG ACT GTG CTG CTC TTG CAG CAG ACT CTG AAA GAA GAG GTT GAG TCC TAT TCC ATC AAA ACC CAG TTT AAC
 N   E   I   N   A   A   W   H   S   G   Q   T   V   L   L   L   Q   Q   T   L   K   M   G   L   Y   C   S   V   P   V   E   W
991/331                                                                                                      1021/341                                                         1051/351
GTT CCT TAC GGA AAC CAT TCA TAT CTA GAG TCT CTG ACA GAC AAA ATG CTT CCG CTT TAC TGT TCT GGG AGT GTT CAG CAG TAC TTT CAG TTT
 V   P   Y   G   N   H   S   Y   L   E   S   L   T   D   K   M   L   P   L   Y   C   S   V   P   V   E   W
1081/361                                                                                                     1111/371                                                         1141/381
TGG GAC AAC AAG TTT GAC CAT GCA ATG GTG GCT TTC CTG GAC TGT GTG CAG CAG TTC AAA GAA GAG GTT GAG AAA GGG GAG GAG TTC
 W   D   N   K   F   D   H   A   M   V   A   F   L   D   C   V   Q   Q   F   K   E   E   V   E   K   G   E   E   F
1171/391                                                                                                     1201/401                                                         1231/411
TGT CTT CCC TAC AGG ATG GAT GTG GAG AAA ATT GAA GAC ACA GGA GGC AGT GGC GGC TCC TAT TCC ATC AAA ACC CAG TTT AAC
 C   L   P   Y   R   M   D   V   E   K   I   E   D   T   G   G   S   G   G   S   Y   S   I   K   T   Q   F   N
1261/421                                                                                                     1291/431                                                         1321/441
TCT GAG GAG CAG TGG ACA AAA GCT CTC AAG TTC ATG CTG ACG AAT CTT AAG TGG GGT CTT GCT TGG GTG TCC TCA CAA TTT TAT AAC AAA
 S   E   E   Q   W   T   K   A   L   K   F   M   L   T   N   L   K   W   G   L   A   W   V   S   S   Q   F   Y   N   K
1351/451
TGA
  *
```

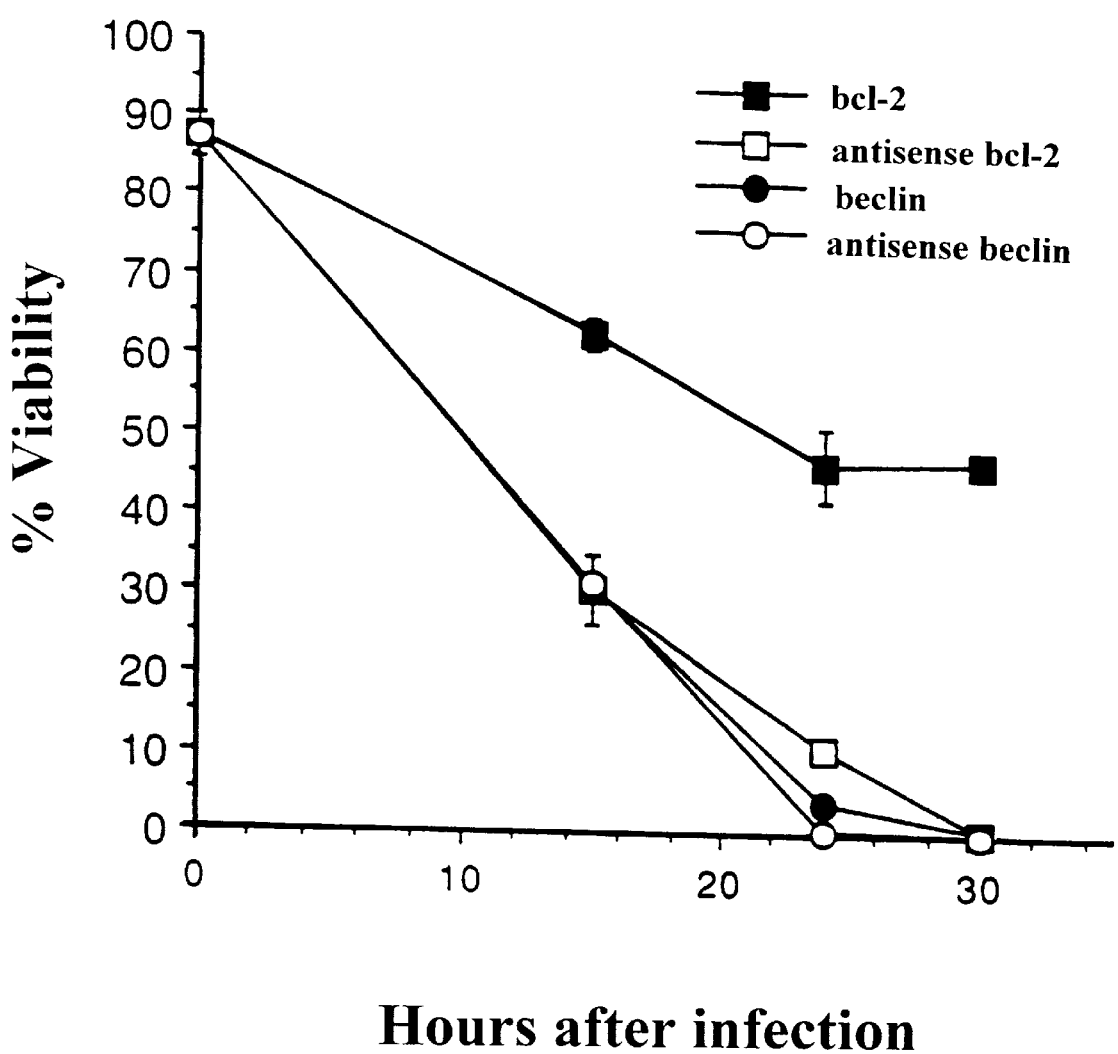

BECLIN-RELATED NUCLEIC ACID MOLECULES, AND USES THEREOF

This application is a §371 of PCT International Application No. PCT/US97/16358, filed Sep. 12, 1997, designating the United States of America, which is a continuation-in-part of U.S. Ser. No. 08/712,939 filed Sep. 13, 1996, now U.S. Pat. No. 5,858,669, the contents of which are incorporated by reference in their entireties into the present application.

The invention disclosed herein was made with Government support under Grant Nos. K08AI01217-01 and R29AI40246 from the National Institutes Of Health of the United States Department of Health and Human Services. Accordingly, the U.S. Government has certain rights in this invention.

BACKGROUND

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

A. Regulation of Apoptosis

1. Apoptosis is important in diverse physiologic processes; the abnormal regulation of apoptosis is important in diverse pathologic processes, including turmorigenesis.

Apoptosis is a highly conserved innate mechanism by which mammalian cells commit suicide. This mechanism allows an organism to eliminate unwanted or defective cells by an orderly process of cellular disintegration, and is characterized by certain stereotypic biochemical (e.g. endonucleosomal cleavage into 180–200 bp multimers) and morphologic features (e.g. chromatin condensation, cytoplasmic blebbing, etc.). Apoptosis plays a role in physiologic processes such as differentiation during embryogenesis, establishment of immune self-tolerance, and killing of cytotoxic immune cells, and apoptosis can be induced in response to a variety of stimuli including DNA damage, growth factor withdrawal, $Ca^{2+}$ influx, ischemia, and viral infection. The unwanted occurrence of apoptosis may play a role in neurodegenerative diseases and aging, and the diminution of apoptotic death may play a role in cancer and chemoresistance.

2. Apoptosis and the cell cycle may share common pathways.

In recent years, the concept that the cell cycle and apoptosis are inextricably linked has gained widespread support in the cell death field. Several different lines of evidence support this concept. For example, in response to different death signals, normally quiescent cells express elevated levels of cell cycle genes (Buttyan, 1991; Freeman, 1994). Oncogenes such as c-myc (Evan, et al., 1996), ras (Wyllie, et al., 1987; Tanaka, et al., 1994) and adenovirus ELA (White, 1991), that promote cell proliferation, also act as triggers of apoptosis. Loss of normal restraints at the G1 checkpoint, such as inactivation of the retinoblastoma gene product, p105Rb (Clarke, et al, 1992; Lee, et al 1992; Jacks, et al, 1992), or deregulated expression of the G1-specific E2F transcription factors (Shan, et al., 1994; Qin, et al., 1994; Wu, et al., 1994) results in uncontrolled proliferation and apoptosis. Loss of the p53 tumor suppressor gene results in resistance to certain apoptotic triggers, and p53 overexpression induces some types of apoptosis (reviewed in Evan, 1995). The morphologic features of apoptosis resemble those of mitotic catastrophe (reviewed in King and Cidlowski, 1995), and premature activation of cyclin dependent kinases is required for some forms of apoptosis (Shi, et al., 1994). Furthermore, several agents that block cell cycle progression also protect neuronal cells from apoptosis induced by withdrawal of trophic factor support (Farinelli and Greene, 1996) and T lymphocytes from apoptosis induced by T-cell receptor ligation (Boehme and Lenardo, 1993). These observations all support the notion of a link between the cell cycle and apoptosis.

3. An evolutionarily conserved set of cellular genes regulate apoptosis.

Several mammalian genes have been identified that function as either inducers (e.g. faslapo-1, bax, ICE-like cysteine proteases, p53) or repressors (e.g. bcl-2, bcl-$x_s$, bcl-$x_L$) of an evolutionarily conserved apoptotic death pathway. Prevailing hypotheses in the cell death field are that a family of ICE-like cysteine proteases (CED-3, ICE, Nedd-2/ICH-1, CPP32) constitute the pivotal triggers of both nematode and mammalian cell suicide program and that a family of bcl-2-related genes constitute the final downstream negative regulators of cell death. Despite the identification of several effectors and repressors of cell death, the precise molecular mechanisms underlining the action of each of these genes remains poorly defined.

4. Bcl-2, the proto-oncogene, inhibits a variety of types of apoptosis.

Bcl-2 (for B cell lymphoma 2) is the prototypic anti-apoptotic gene. It was first discovered by virtue of its involvement in the t(14:18) chromosomal translocations found in the majority of non-Hodgkin's B cell lymphomas (Tsujimoto and Croce, 1985). Bcl-2 can prevent or delay apoptosis induced by a wide variety of stimuli (reviewed in Park and Hockenbery, 1996), including growth factor deprivation, alterations in $Ca^{2+}$, free radicals, cytoxic lymphokines, some types of viruses, radiation and most chemotherapeutic drugs. The ability of Bcl-2 to inhibit apoptosis induced by such diverse stimuli suggests that this oncoprotein controls a common final pathway involved in cell death regulation.

5. Dysregulated Bcl-2 expression occurs in a wide variety of human cancers and contributes to neoplastic cell expansion.

While the bcl-2 gene was first discovered because of its involvement in t(14:18) translocations found frequently in non-Hodgkin's lymphomas, high levels and aberrant patterns of bcl-2 gene expression have been reported in a wide variety of human cancers, including colorectal, gastric, prostate, non-small cell lung, neuroblastomas, breast and ovarian cancer (reviewed in Reed, et al., 1996). In these tumors, it is thought that Bcl-2 contributes to neoplastic cell expansion by preventing cell turnover caused by physiological cell death mechanisms. In addition to its role in the development of human tumors, high levels of Bcl-2 expression are thought to play an important role in the resistance of tumor cells to cytotoxic anticancer drugs and radiation.

6. The mechanism by which Bcl-2 inhibits apoptosis is still poorly understood.

Several potential mechanisms of action have been proposed for Bcl-2, including protection against oxidative stress (Hockenbery et al., 1993; Kane et al., 1993), regulation of intracellular $Ca^{2+}$ homeostasis (Lam, et al., 1993), antagonism of cell death proteases (e.g. ICE-like family of cysteine proteases) (Miura, et al., 1993) and other cell death effectors (e.g. bax) (Yin, et al., 1994), and association with the signal transducing proteins, R-ras and Faf-1 (Fernandez-Sarbia and Bischoff, 1993; Wang, et al., 1994). In addition, two recent reports have suggested that Bcl-2 may exert anti-apoptotic effects by delaying cell cycle progression (Mazel, et al., 1996; Borner, 1996). Despite these numerous proposed mechanisms, there is considerable contradictory evidence and no universal agreement in the cell death field as to how Bcl-2 actually works. Further elucidation of the precise mechanism(s) of action of Bcl-2 is a high research priority in the field.

7. No functional links have been identified between inhibitors of apoptosis and inhibitors of cell cycle.

According to the concept that the cell cycle is linked to apoptosis, one would predict that cellular genes that inhibit apoptosis would be functionally linked to genes that exert effects on the cell cycle. Along these lines, Bcl-2 has been shown to delay cell cycle progression (as stated above), and Bcl-2 has also been postulated to function as a nuclear "gatekeeper" that regulates nuclear access of cyclin-dependent kinases. However, to date, Bcl-2 has not been shown to directly interact with any proteins that affect the cell cycle.

8. Further investigation of the mechanism(s) underlaying the death repressor activity of Bcl-2, including the characterization of novel Bcl-2 interacting proteins, will provide new insights into apoptosis and diseases in which apoptosis plays a pathogenetic role.

Understanding how Bcl-2 inhibits cell death is a critical question that has important implications for an understanding of all physiologic processes that involve cell death.

B. Molecular Pathogenesis of Breast and Ovarian Cancer

1. Several genes are responsible for inherited breast and ovarian cancer.

The existence of one gene predisposing to breast and ovarian cancer on chromosome 17q21, BRCA1, was proven by linkage analysis several years ago (Hall, et al., 1990), and isolated in 1994 by positional cloning (Miki, et al., 1994; Futreal, et al., 1994). BRCA1 is mutated in the germline and the normal allele is lost in tumor tissue from approximately 50% of cases of hereditary breast and ovarian cancer (reviewed in Szabo and King, 1996). BRCA2, a second breast cancer susceptibility gene, has been mapped to chromosome 13q21 and is presently implicated in 20% of hereditary cases (reviewed in Szabo and King, 1996). At least two other genes, p53 and the androgen receptor are also responsible for inherited predisposition to breast cancer in families. Other epidemiologic studies have suggested that carriers of mutations in the ataxia telangieclasia gene and HRAS1 minisatellite locus are also at increased risk of breast cancer.

2. Molecular genetic evidence suggests chromosome 17q21 may contain a second tumor suppressor tumor suppressor gene (in addition to BRCA1) that is important in sporadic breast and ovarian cancer.

Allelic deletions of chromosome 17q21 (loss of heterozygosity [LOH] that include that BRCA1 region are found to occur in 50–70% of breast carcinomas (Futreal, et al., 1992; Cropp, et al., 1993; Saito, et al., 1993) and in up to 75% of ovarian carcinomas (Russell, et al., 1991; Sato, et al., 1991; Eccles, et al., 1991; Yang-Feng, et al., 1993). However, while several studies have confirmed the role of germline BRCA1 mutations in hereditary breast and ovarian cancers (Miki, et al., 1994; Futreal, et al., 1994), somatic mutations in BRCA1 have been found in very few cases of sporadic cancers (Futreal, et al., 1994; Takahashi, et al., 1995; Merajver, et al., 1995; Hosking, et al. 1995). This raises the strong possibility that the frequent allelic loss on chromosome 17q21 in sporadic breast and ovarian cancer reflects the involvement of an additional tumor suppressor gene. In further support of this hypothesis, more detailed deletion mapping of sporadic epithelial ovarian carcinomas has revealed a common deletion unit, located on chromosome 17q21 that is located approximately 60 kb centromeric to BRCA1 (Tangir, et al., 1996). Thus, the presence of LOH in sporadic ovarian cancer cases of a region of chromosome 17q21 that does not encompass BRCA1 may reflect the presence of an additional tumor suppressor gene.

C. Overview

In response to different death signals, normally quiescent cells express elevated levels of cell cycle genes (Buttyan, R., 1991; Freeman, R. S., et al., 1994) Oncogenes, such as c-myc (Evan, G. J., 1992), ras (Wyllie, A. H., et al. (1987; Tanaka, N., et al., 1994), and adenovirus E1A (White, E., et al., 1991), that promote cell proliferation, also act as triggers of apoptosis. Loss of these restraints at the G1 checkpoint, such as inactivation of the retinoblastoma gene product, p105Rb (Clarke, A. R., et al., 1992; Lee, E-H., et al. (1992; Jacks, T., et al., 1992), or deregulated expression of the G1-specific E2F transcription factors (Shan, B., et al., 1994; Qin, X., et al. 1994; Wu, X. and Levine, A. J., 1994), results in uncontrolled proliferation and apoptosis. The p53 tumor suppressor gene enforces cell cycle arrest or apoptosis following DNA damage and also mediates apoptosis triggered by a variety of non-genotoxic stimuli (reviewed in Evan, G. I., et al., 1995). The morphologic features of apoptosis resemble those of the mitotic catastrophe (reviewed in King, K. L., et al., 1995), and premature activation of cyclin-dependent kinases is required for some forms of apoptosis (Shi, L., et al., 1994). Furthermore, phamacologic and genetic inhibitors of cell cycle progression protect many cell types from apoptosis (Farinelli, S. E., et al., 1996; Meikrantz, W. and Schlegel, R., 1996). These observations all suppport the notion that regulation of the cell cycle is intricately involved in cell death.

According to this notion, cellular genes that inhibit apoptosis may be functionally linked to genes that exert effects on the cell cycle. Consistent with this hypothesis, the death-protective activity of Bcl-2, the prototype member of a family of cell death regulators, is associated with a delay in the kinetics of cells cycle progression (Borner, C., 1996; Mazel, S., et al., 1996; O'Reilly, L. A., et al., 1996; Vairo, B., et al. 1996). Furthermore, Bcl-2 overexpression suppresses NF-AT signalling and activation of T-cells (Linette, G. P., et al., 1996; Shibasaki, F., et al., 1997). Such findings suggest that regulators of cell death can affect cellular proliferation pathways. However, it is, as yet unknown, whether interactions between cell death regulators and cellular proliferation pathways are mechanistically important in the death repressor activity of anti-apoptotic genes.

To further understand the mechanism by which bcl-2 protects against apoptosis, the yeast hybrid system was used to screen a mouse brain library for complementary cDNAs encoding proteins that bind to Bcl-2. The yeast two hybrid system has proven useful to identify interactions between Bcl-2 and novel proteins (Fernandez-Sarbia, M. J., et al., 1993; Boyd, J., et al., 1994; Yang, E., et al., 1995; Farrow, S. N., et al., 1995), to analyze hetero-and homodimerization of Bcl-2 family members (Sato, T., et al., 1994; Sedlack, T. W., et al., 1995), and to perform structure-function analysis of the Bcl-2 protein.

SUMMARY OF THE INVENTION

This invention provides for an isolated nucleic acid which encodes a wildtype human Beclin. This invention also provides for a mutant human Beclin.

This invention also provides for a vector comprising the isolated nucleic acid which encodes a wildtype human Beclin operatively linked to a promoter of RNA transcription, specifically, the plasmid pSG5/beclin.

This invention also provides a method of obtaining a polypeptide in purified form, specifically a wildtype human Beclin. This invention also provides for purified wildtype human Beclin.

This invention also provides for an oligonucleotide of at least 15 nucleotides capable of specifically hybridizing with a unique sequence of nucleotides within a nucleic acid which encodes a wildtype Beclin without hybridizing to any sequence of nucleotides within a nucleic acid which encodes a mutant human Beclin. This invention also provides for an oligonucleotide of at least 15 nucleotides capable of specifically hybridizing with a unique sequence of nucleotides within a nucleic acid which encodes a mutant Beclin without hybridizing to any sequence of nucleotides within a nucleic acid which encodes a wildtype human Beclin.

This invention also provides for a method for detecting a mutant human Beclin in a subject. This invention also provides for a method for determining whether a subject has a predisposition for cancer. Further, this invention also provides a method for determining whether a subject has cancer.

This invention also provides a method for inhibiting cell proliferation in cells unable to regulate themselves.

This invention also provides a pharmaceutical composition comprising a wildtype human Beclin and a pharmaceutically acceptable carrier.

This invention also provides for a method for treating a subject who has cancer.

This invention also provides for a method for detecting the presence of human chromosomal region 17q21 in a sample of genomic DNA.

This invention also provides a method for treating a subject unable to control apoptosis in the cells of the subject.

BRIEF DESCRIPTION OF THE FIGURES

FIGS. 1A and 1B. Deduced amino acid sequence and nucleotide sequence of human beclin.

1A. The deduced amino acid sequence (Seq. I.D. No.: 1) was used to scan various data banks. The boxed area represents the Bcl-2 binding domain of human Beclin (see Table 1) and the underlined area corresponds to the region that is predicted to have a coiled-coil conformation.

1B. The nucleotide sequence of human Beclin (Sequence I.D. No.: 2). The partial nucleotide sequence of mouse Beclin obtained from sequencing clone F1 was aligned with an overlapping clone GT197 isolated from human breast (Rommens, 1995). Primers immediately upstream and downstream of the predicted open reading frame were used to amlify the coding sequence of human beclin from a normalized human infant brain cDNA library (Soares, M. B., et al., 1994).

Figure 2A:
Figure 2B:
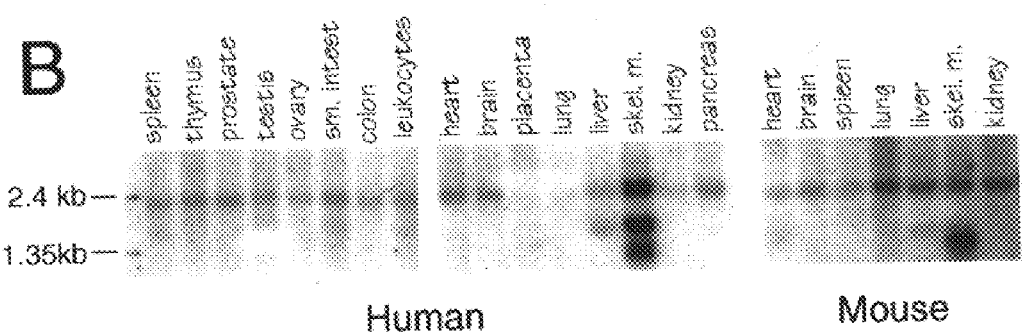
Figure 2C:
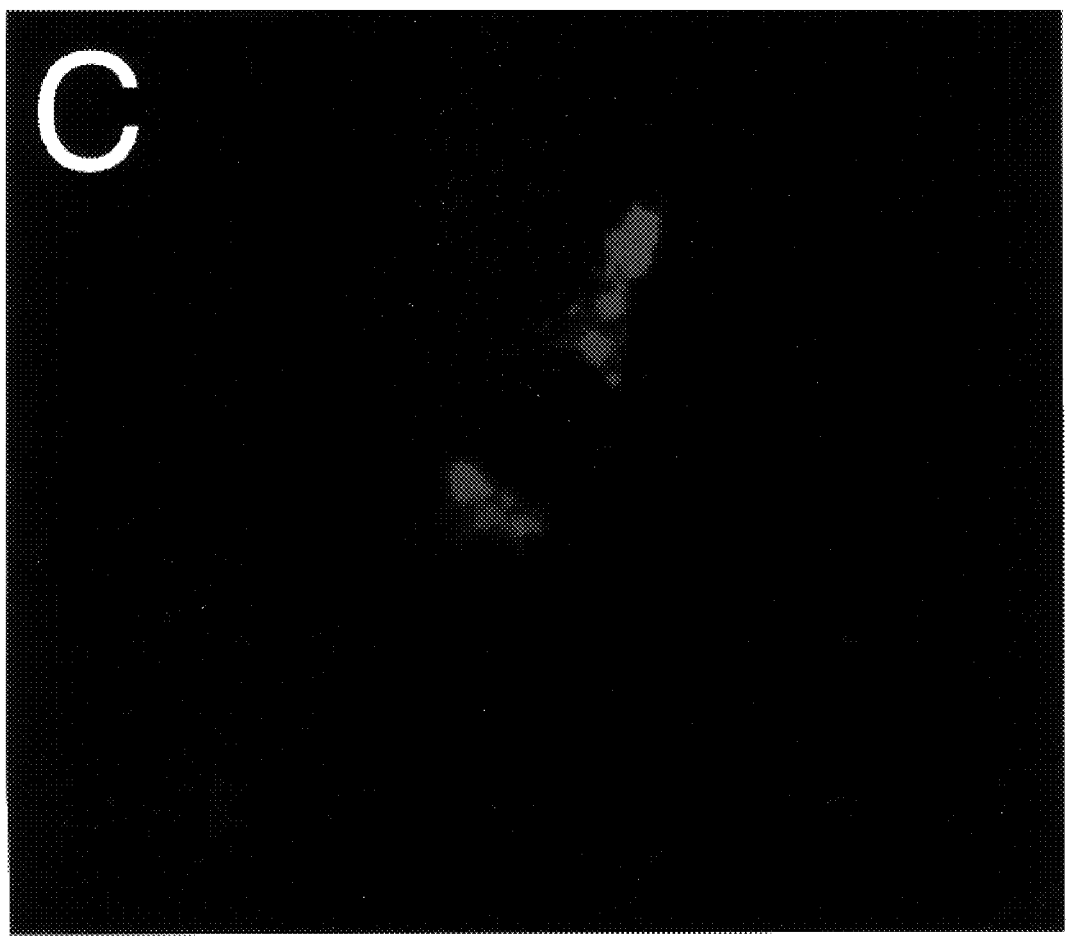
Figure 2D:
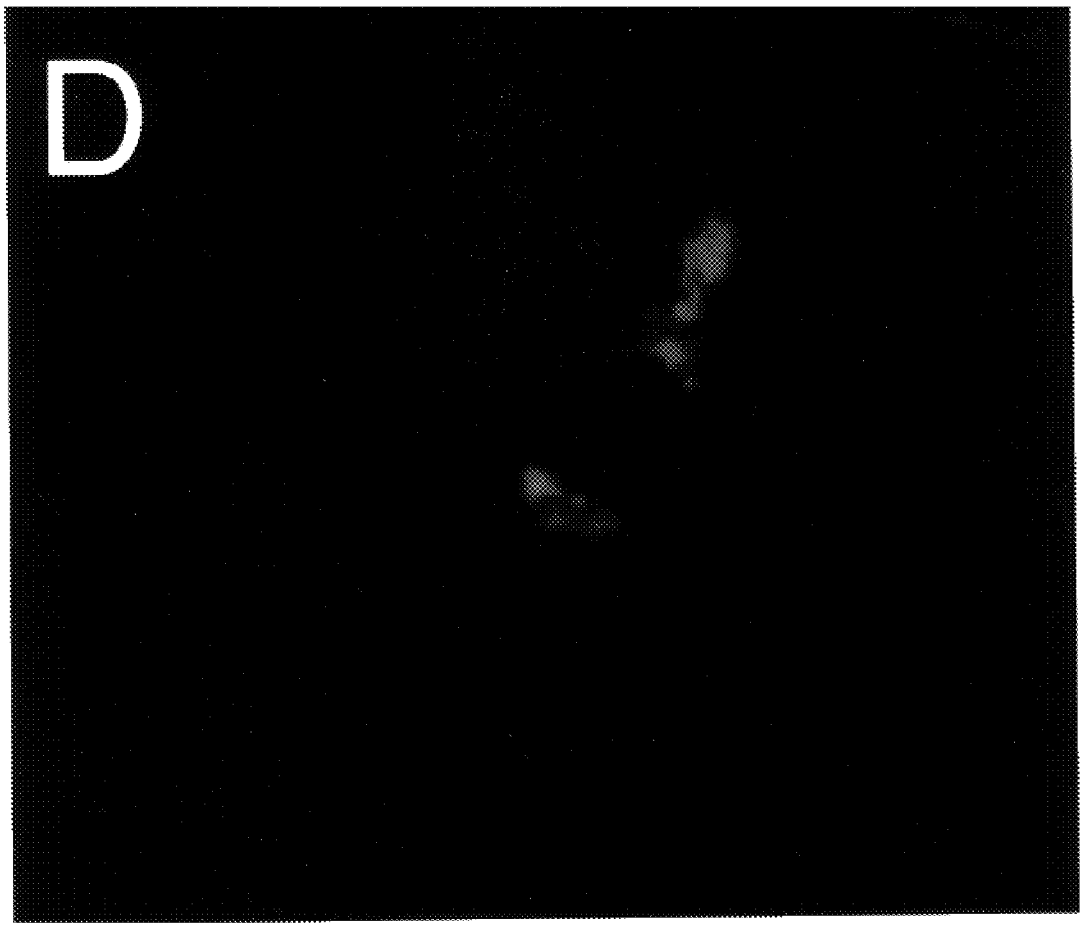
Figure 3A:
Figure 3B:
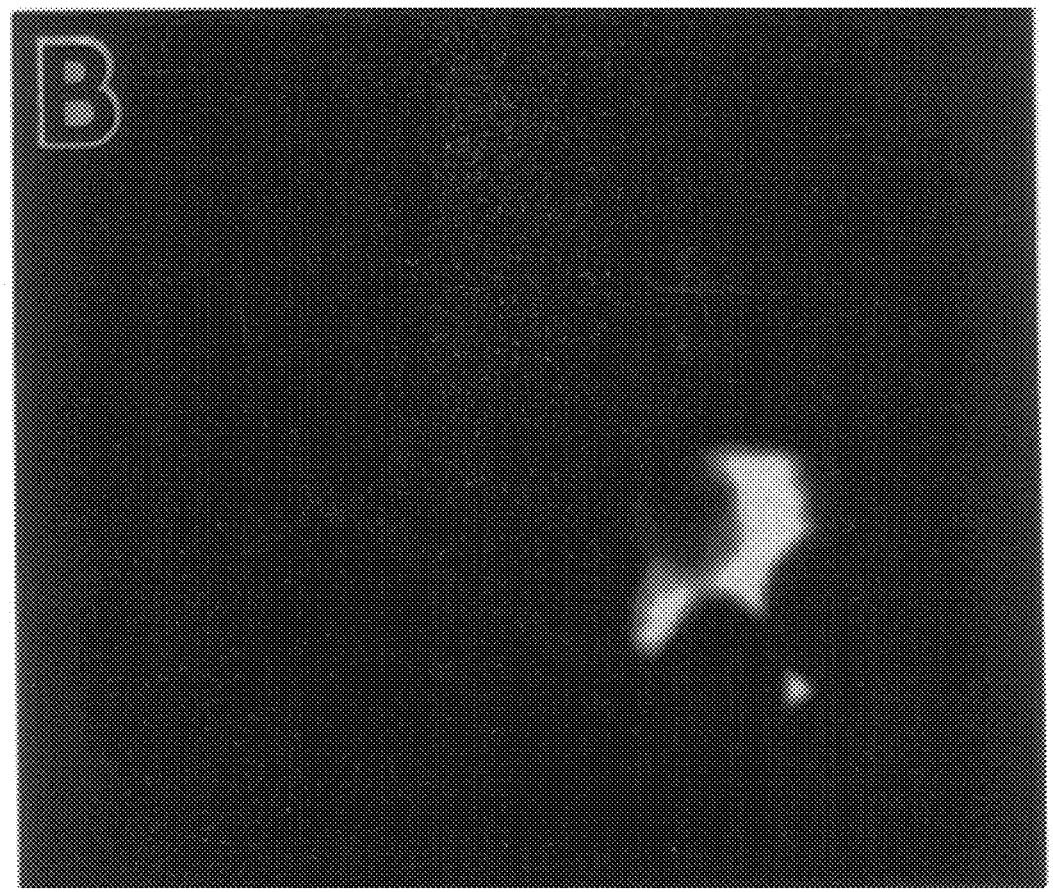
Figure 3C:
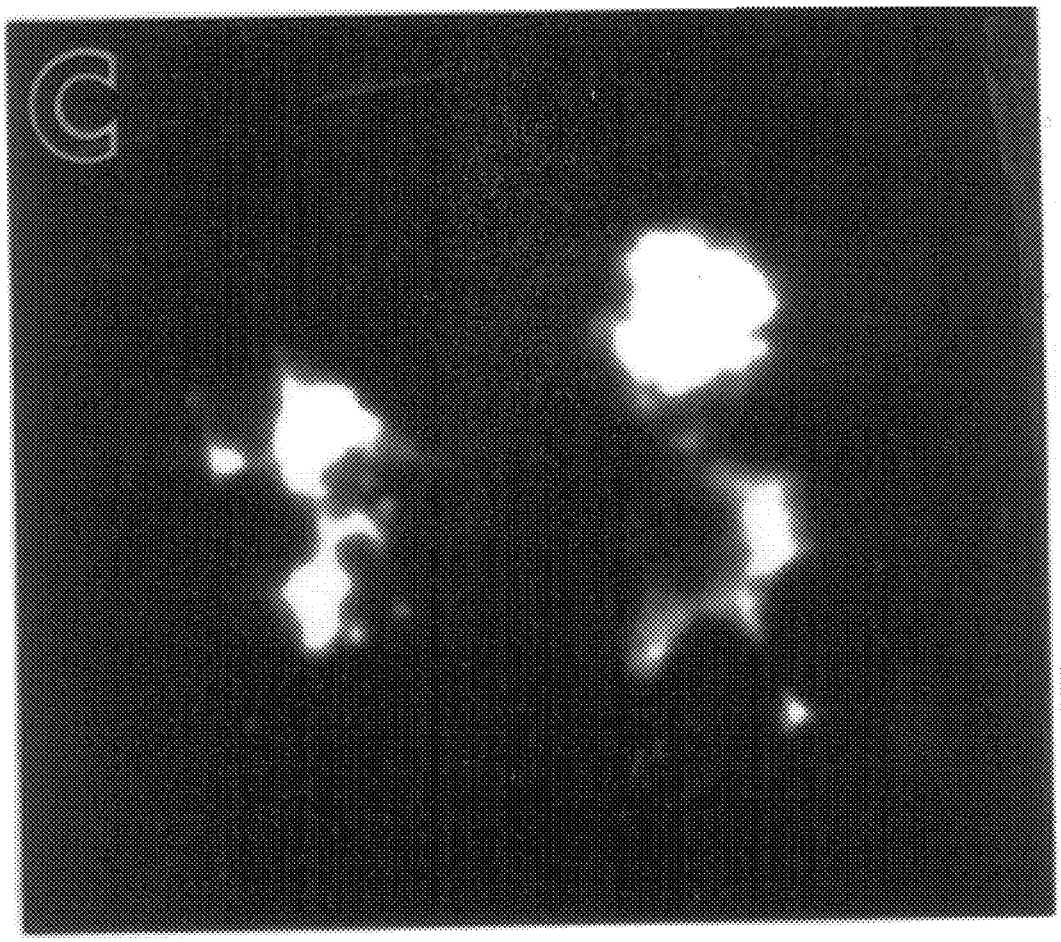
Figure 3D:
Figure 3E:
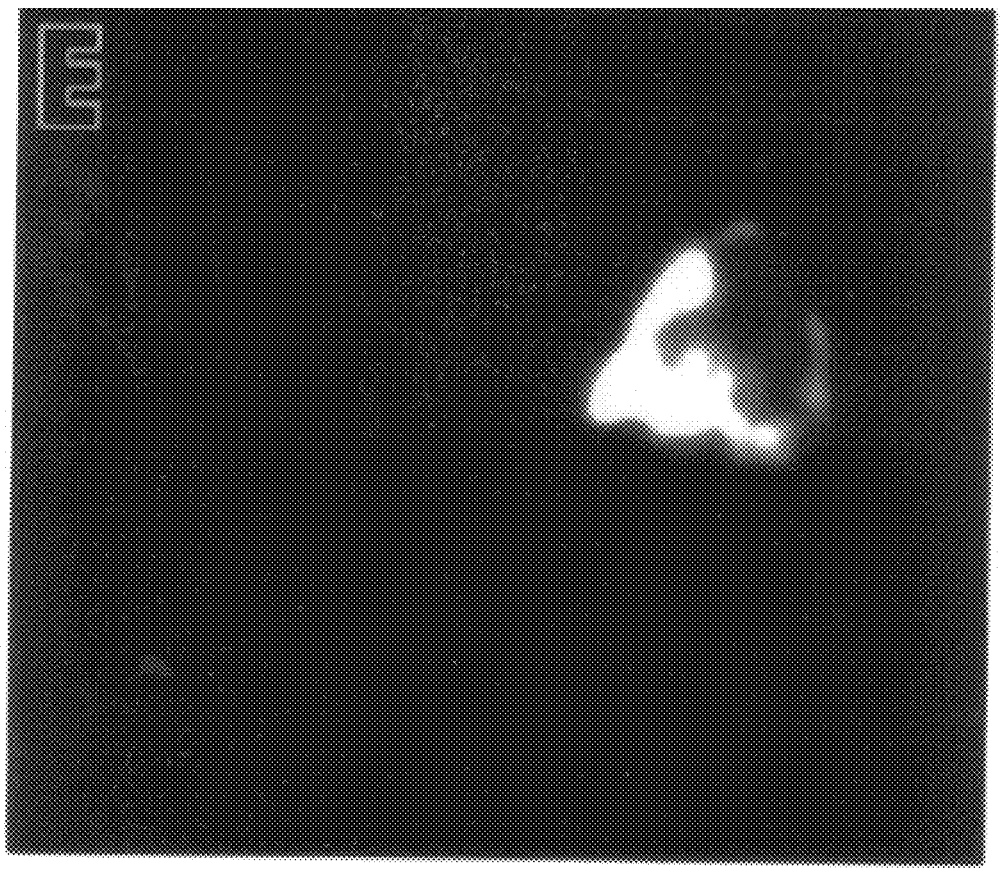
Figure 3F:
Figure 3G:
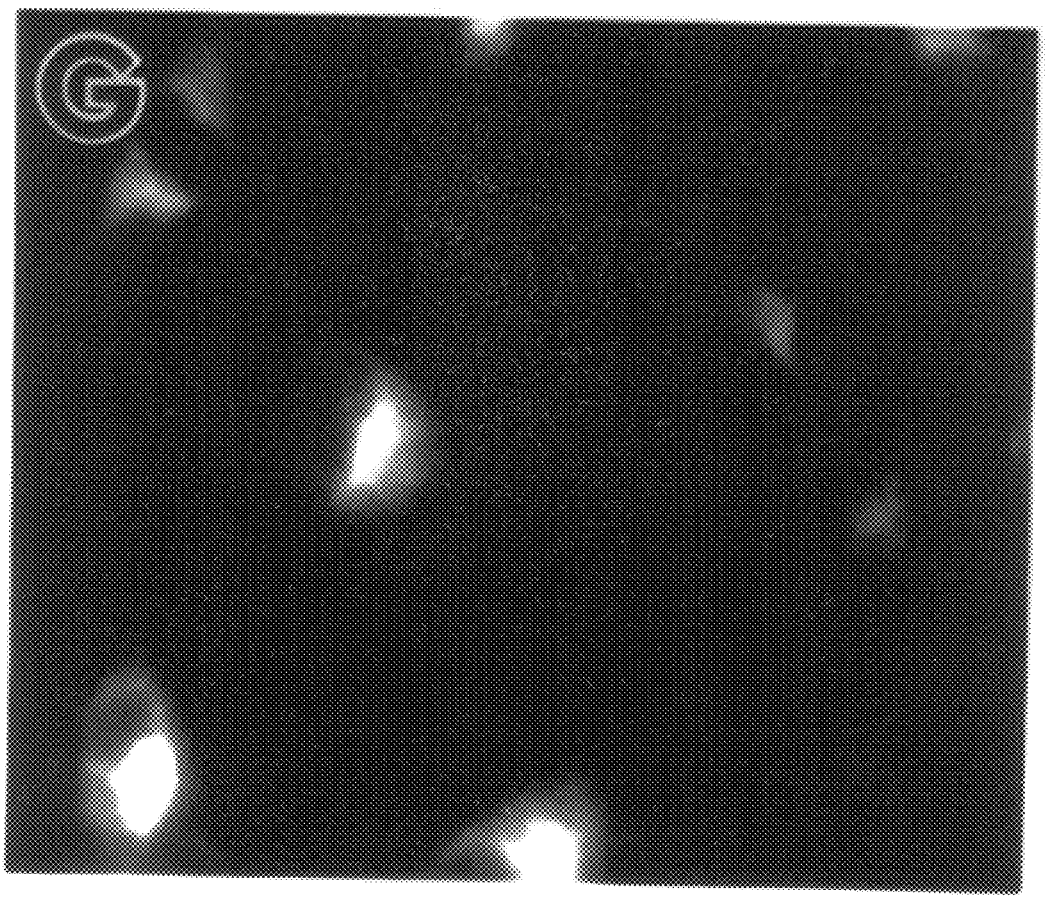
Figure 3H:
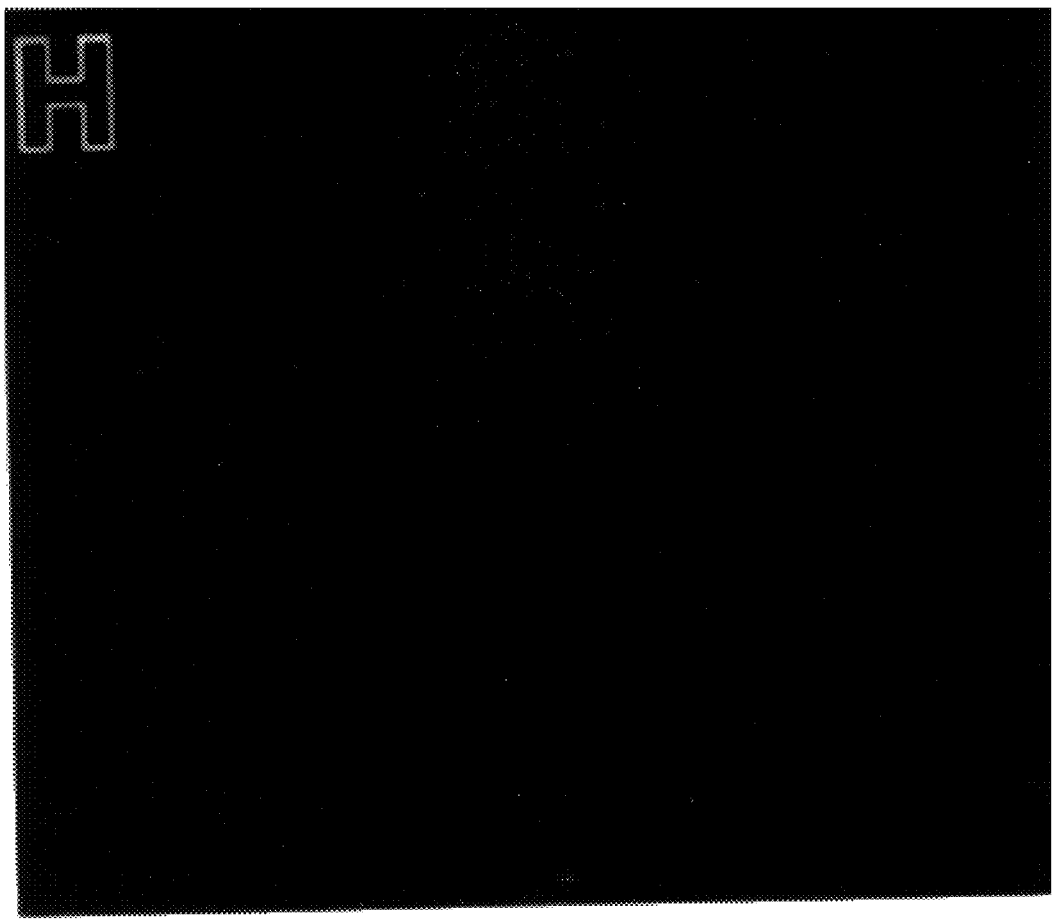
Figure 3I:
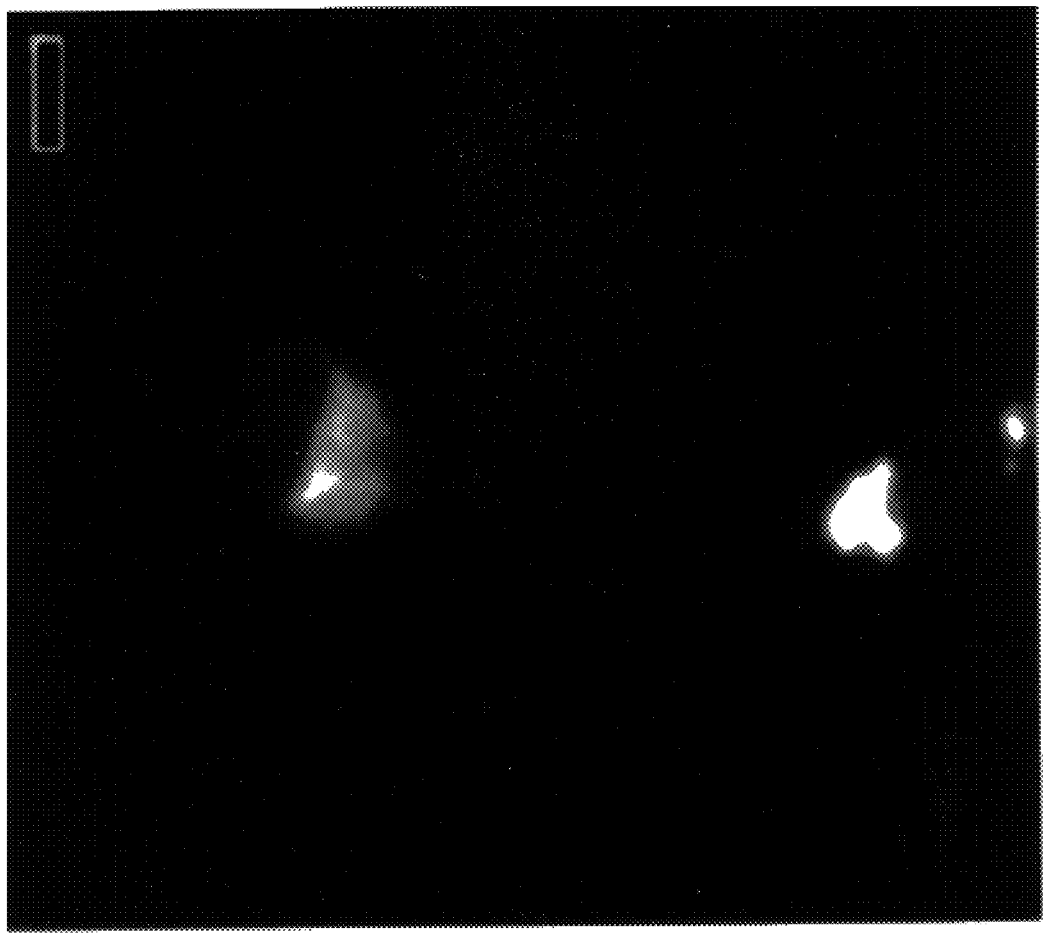

FIGS. 2A, 2B, 2C and 2D. Beclin mRNA and protein expression. For FIGS. 2C and 2D, cells were co-transfected with 4 μg of pSG5/human bcl-2 and 4 μg of pSG5/beclin using lipofectin and fixed after 48 hours with 100% ETOH. Beclin expression was detected with a monoclonal anti-flag M2 Ab (1:20) and FITC-conjugated horse anti-mouse IgG Ab and Bcl-2 expression was detected with a polyclonal rabbit anti-Bcl-2 Ab and rhodamine-conjugated goat anti-rabbit Ab. Individual co-transfected cells were analyzed with confocal laser microscopy. In FIGS. 2C and 2D, equal amounts of loading (2 μg of poly A) were confirmed by hybridization to a B-actin probe.

2A. Western blot analysis of cell lysates prepared from BHK cells infected with a recombinant Sindbis virus chimera containing a flag epitope tagged human beclin insert (lane 2) or a control recombinant Sindbis virus chimera (lane 1) and probed with an anti-flag antibody M2 antibody (IBI) using well-known methods.

2B. Northern blot analysis of beclin mRNA expression in human and mouse tissues. Human and mouse multiple tissue blots (Clontech) were hybridized respectively, according to manufacturer's instructions (Clontech) with a $^{32}$P-labeled 485 base pair probe corresponding to nucleotides 1–485 of human or mouse beclin. Beclin-specific probes hybridized to 2.3 kb transcripts in all examined tissues.

2C. Immunofluorescence staining of human bcl-2 in a BHK cell.

2D. Immunofluorescence staining of human beclin in the same BHK cell shown in FIG. 2C.

FIGS. 3A–3I. Interactions of Bcl-2 and Beclin in vivo demonstrated using FRET microscopy. For the experimental cells, there were three types of labeling: acceptor and donor (n=7), donor alone (n=10), and acceptor alone (n=10). Each labeling type was imaged using the three filter sets: the donor filter set, the acceptor filter set, and the combination set (i.e. FRET set) which best detects the FRET signal. Several cells of each type were imaged so that there were many possible triplets of cells consisting of one each of acceptor plus donor, donor alone and acceptor alone. All possible triplets were analyzed; triplets which generated divide by zero erros or negative energy transfers were excluded. The same method was applied to the control cells where there were 13 acceptor plus donor cells, 10 donor cells alone and 10 acceptor cells alone.

3A. 3D. 3G. Donor (FITC) filter set.

3B, 3E, 3H. FRET filer set.

3C, 3F, 3I. Acceptor (Rhodamine) filter set.

3A–3F Cos cells co-transfected with flag epitope-tagged Beclin and Bcl-2, labeled with anti-flag (donor, FITC) and anti-Bcl-2 (acceptor, Rhodamine) specific antibodies, respectively. 3G–3I Cos cells transfected with Bcl-2 labeled with antibodies against SERCA (Research Design, Inc.) (donor, FITC) and Bcl-2 (acceptor, Rhodamine). Cos cells were co-transfected with pSG5/flag-Beclin and pSG5/BCL-2, labled as in FIGS. 2C and 2D, and FRET microscopy was performed as described herein.

Figure 4B:
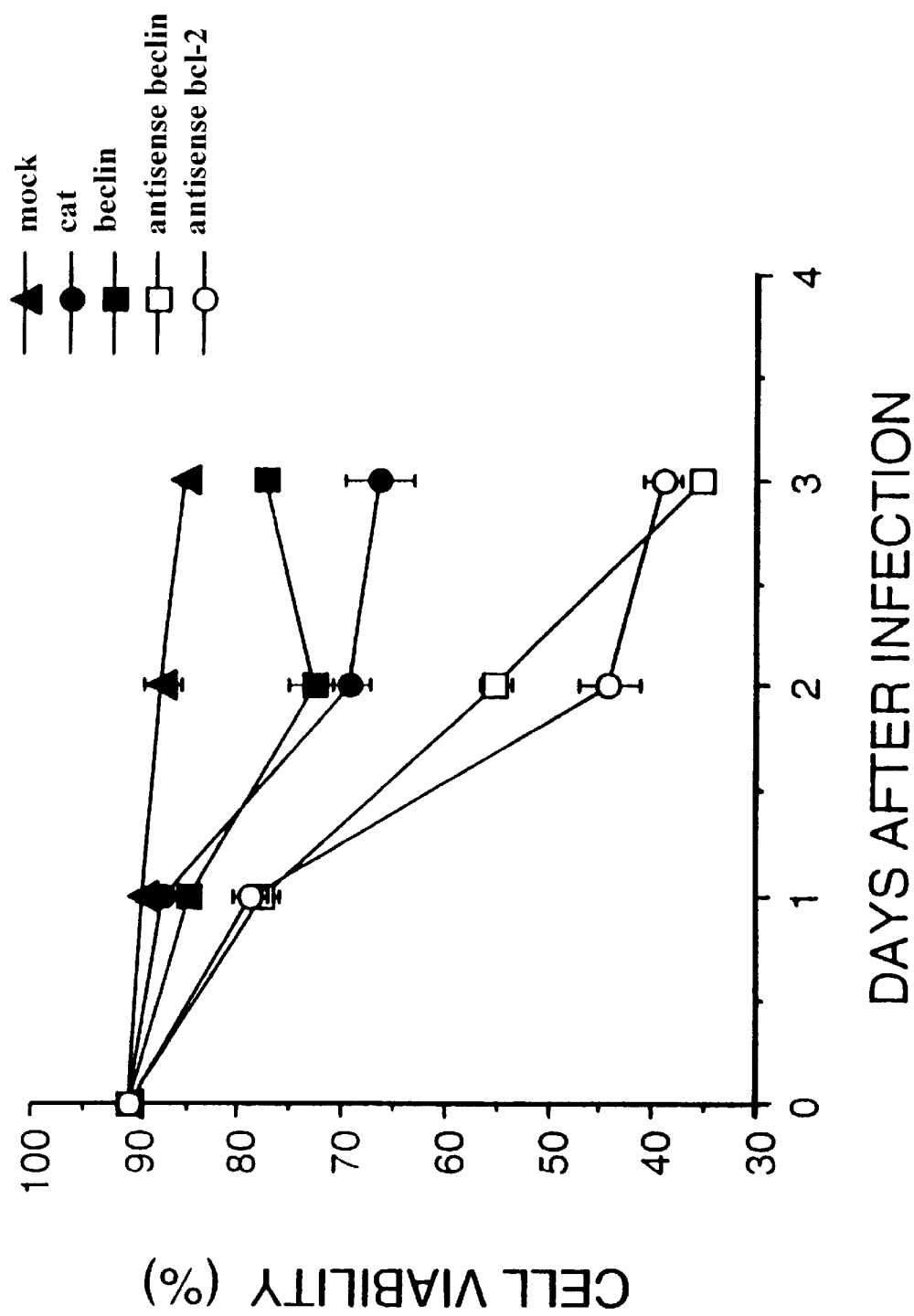
Figure 4C:
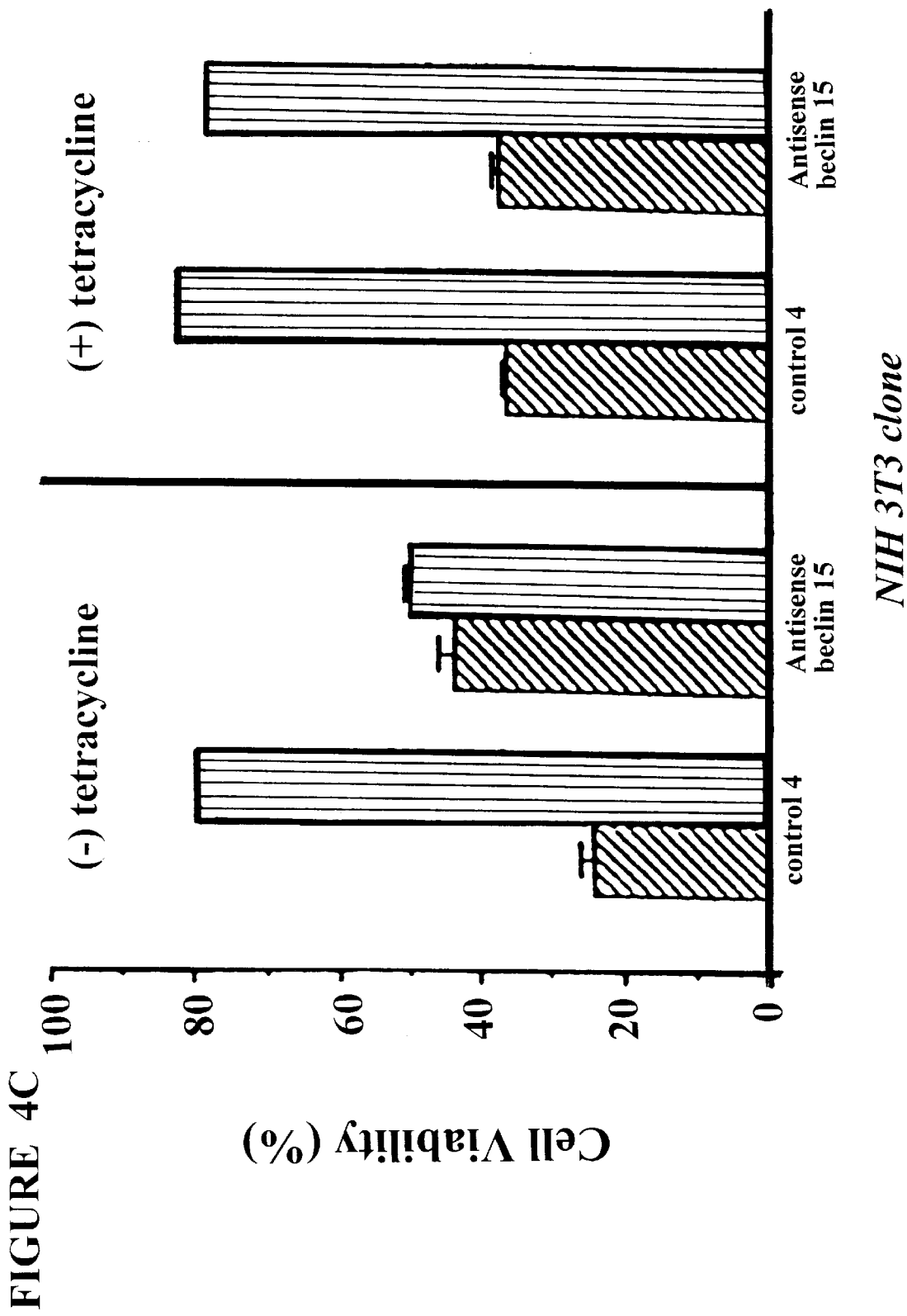

FIGS. 4A–4C. Effect of beclin and antisense beclin on Sindbis virus-induced apoptosis. Recombinant chimeric viruses SIN/antisense bcl-2, SIN/antisense beclin were constructed using methods described for the construction of SIN/flag-beclin and infected at a multiplicity of infection (MOI) of one plaque-forming unit per cell. Cell viability was determined by trypan blue exclusion at serial time points after infection in FIG. 4A and FIG. 4B, and at 24 hours after infection in FIG. 4C. The results of triplicate wells are shown (mean=S.E.) Similar results were obtained in more than 5 independent experiments for FIG. 4A and FIG. 4B and in three independent experiments in FIG. 4C.

4A. Cell viability of BHK cell death after infection with recombinant Sindbis viruses containing bcl-2 in either the sense (SIN/bcl-2) or antisense orientation (SIN/antisense bcl-2) or beclin in either the sense (SIN/beclin) or antisense orientation (SIN/antisense beclin).

4B. Cell viability of AT3/Bcl-2 cells after infection with SIN/CAT, SIN/beclin, SIN/antisense beclin, or SIN/antisense bcl-2.

4C. Cell viability of NIH 3T3 antisense beclin and NIH 3T3 control cells after infection with Sin/bcl-2 (shaded bars) or SIN/bcl-2 stop (hatched bars) in the presence or absence of tetracycline. NIH 3T3 clones were cultured for three days in the presence or absence of 1 μg/ml tetracycline prior to infection.

Figure 5A:
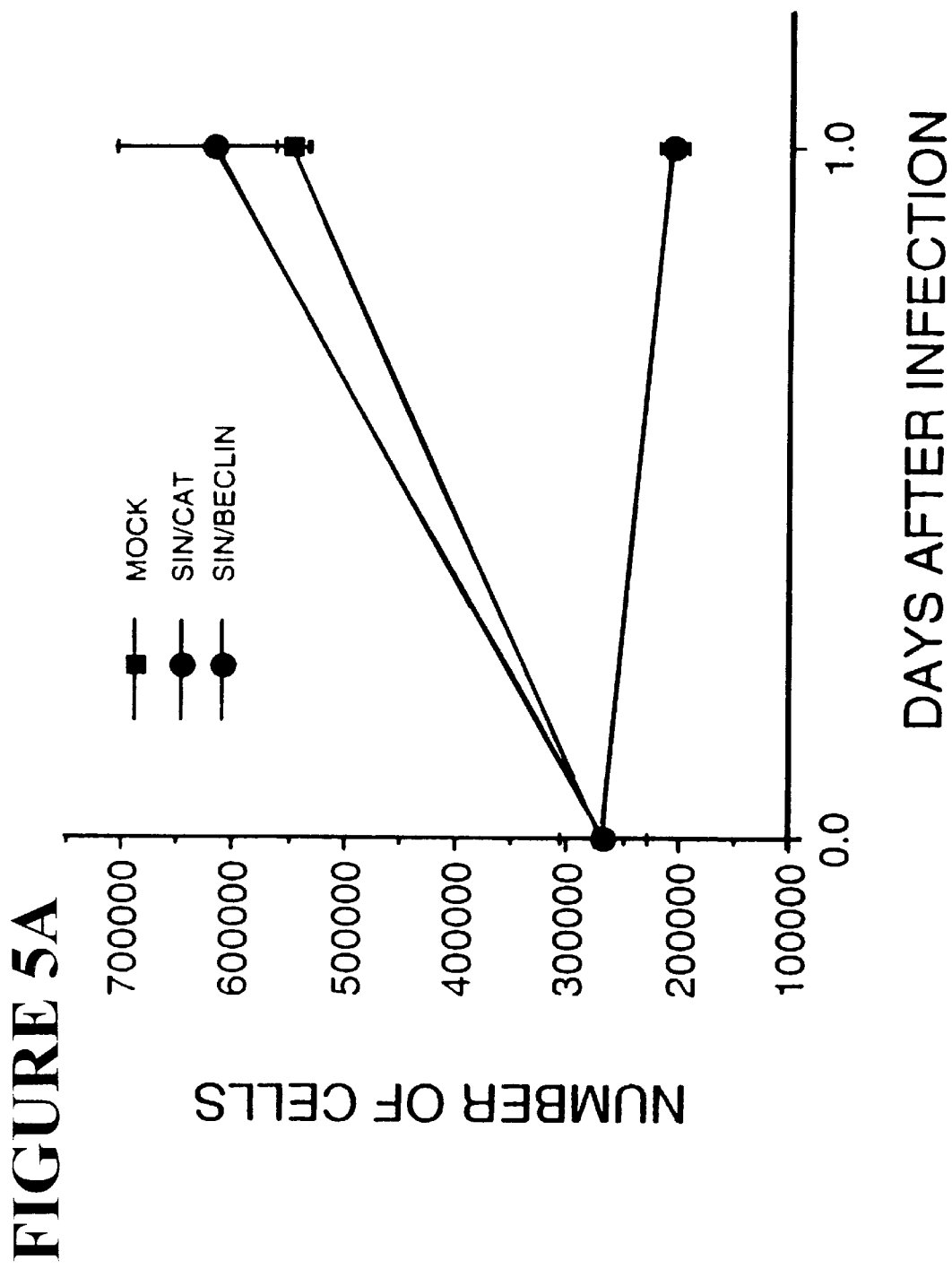
Figure 5B:
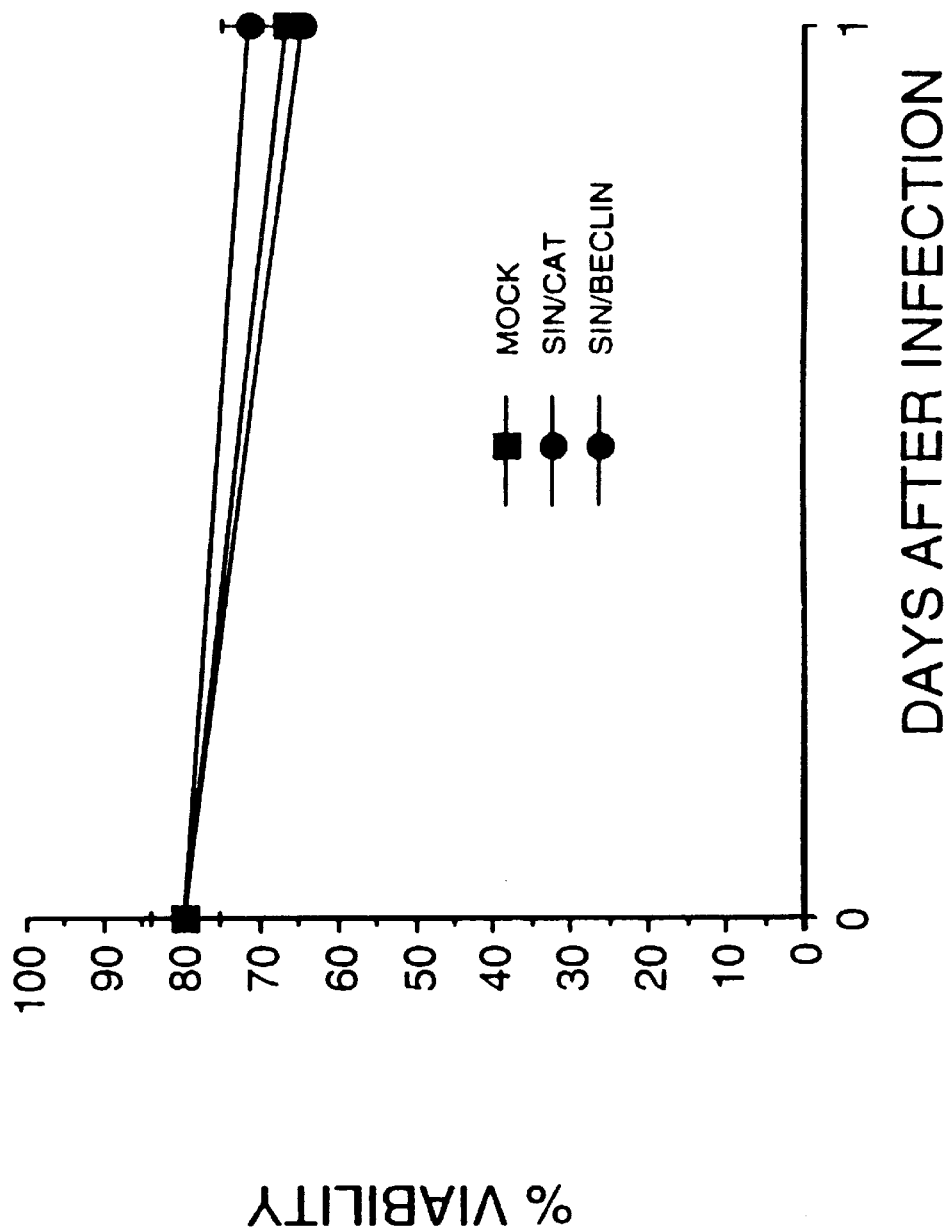
Figure 5C:
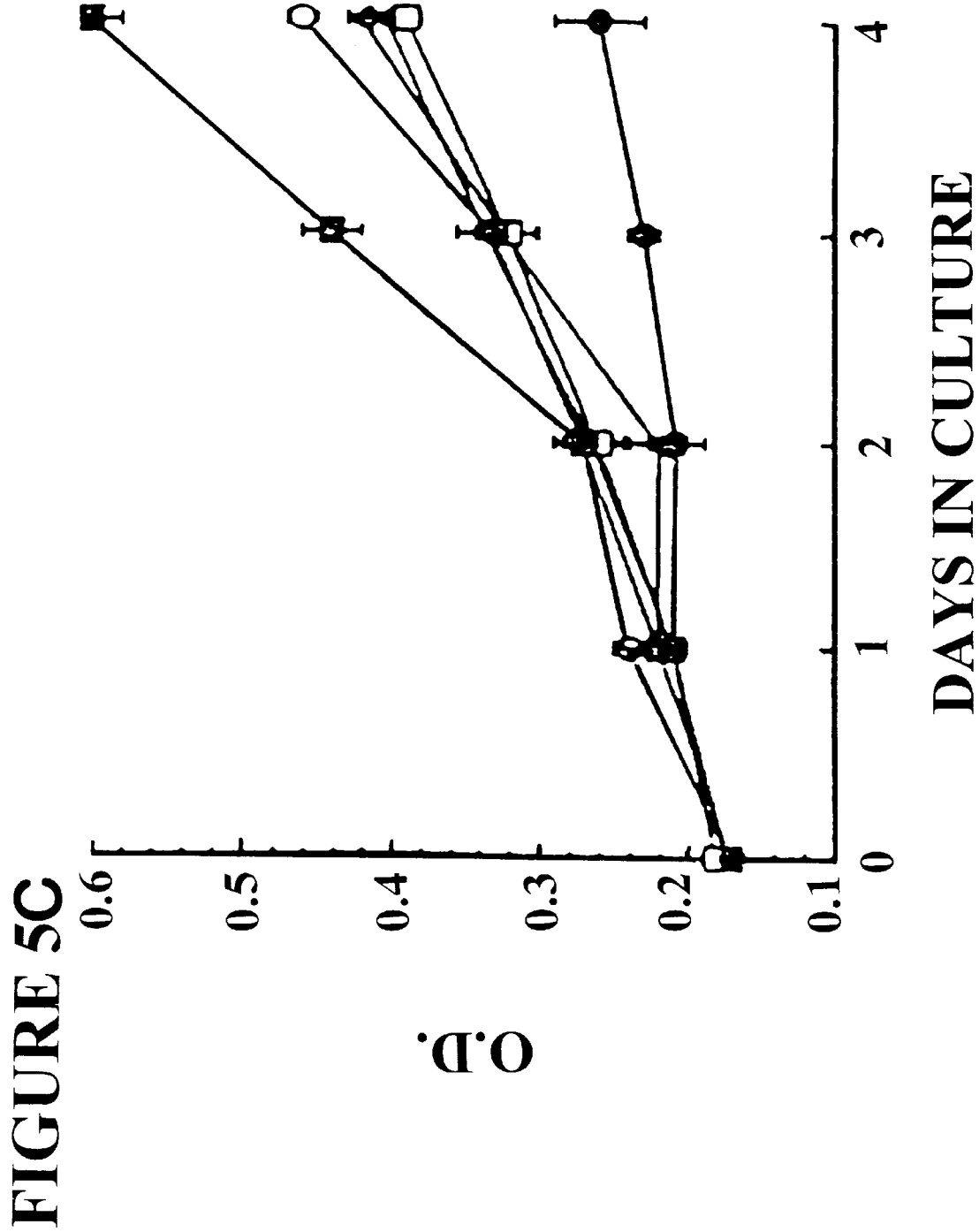

FIGS. 5A–5C. Effect of beclin on AT3 and mouse fibroblast NIH 3T3 cellular proliferation. For FIGS. 5A and 5B, 5×10$^5$ cells were seeded in 35 mm wells, and 24 hours later, infected at a MOI of 1. Results are presented as means±s.e. For FIG. 5C, cells were cultured for three days± tetracycline prior to seeding 5×10 cells/well in 96 well plates. At several time points in culture, cells proliferation was measured by performing MTT assays (MTT proliferation kit, Boehringer Mannheim) according to the manufacturer's instructions. Results are presented as mean O.D.±s.e for triplicate wells. Similar results were obtained in three independent experiments.

5A. Determination of total cell number of AT3/bcl-2 cell number.

5B. Determination of percentage of cell viability of AT3/blc-2 cell viability after infection with SIN/CAT (open circles), SIN/beclin (solid circles) or mock infection (solid squares).

5C. NIH beclin clone 10 (circles), NIH antisense beclin clone 15 (squares) and NIH control clone 4 (triangles) proliferation in the presence (open symbols) or absence (cloned symbols) of tetracycline.

Figure 6A:
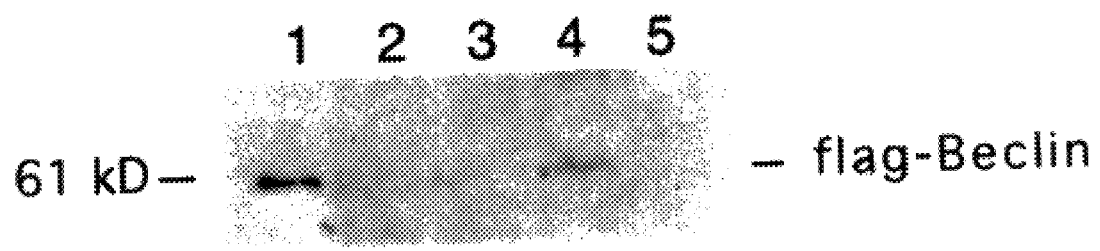
Figure 6B:
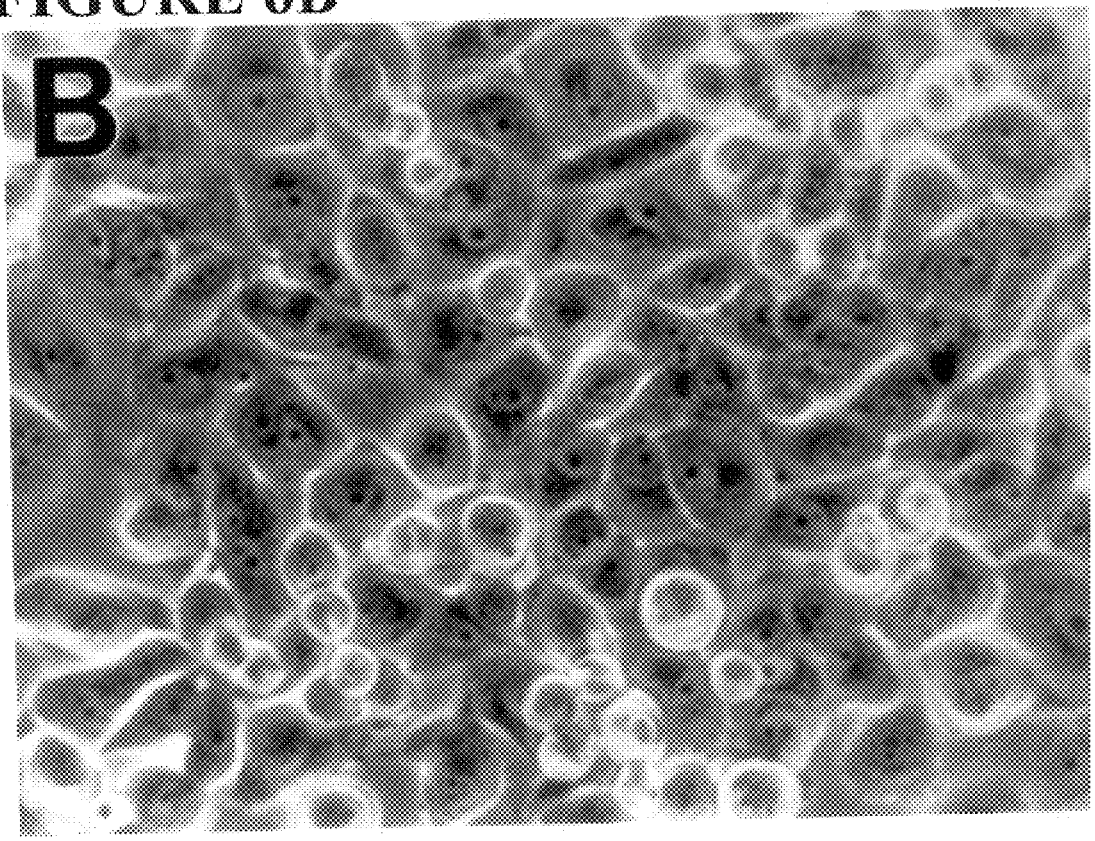
Figure 6C:
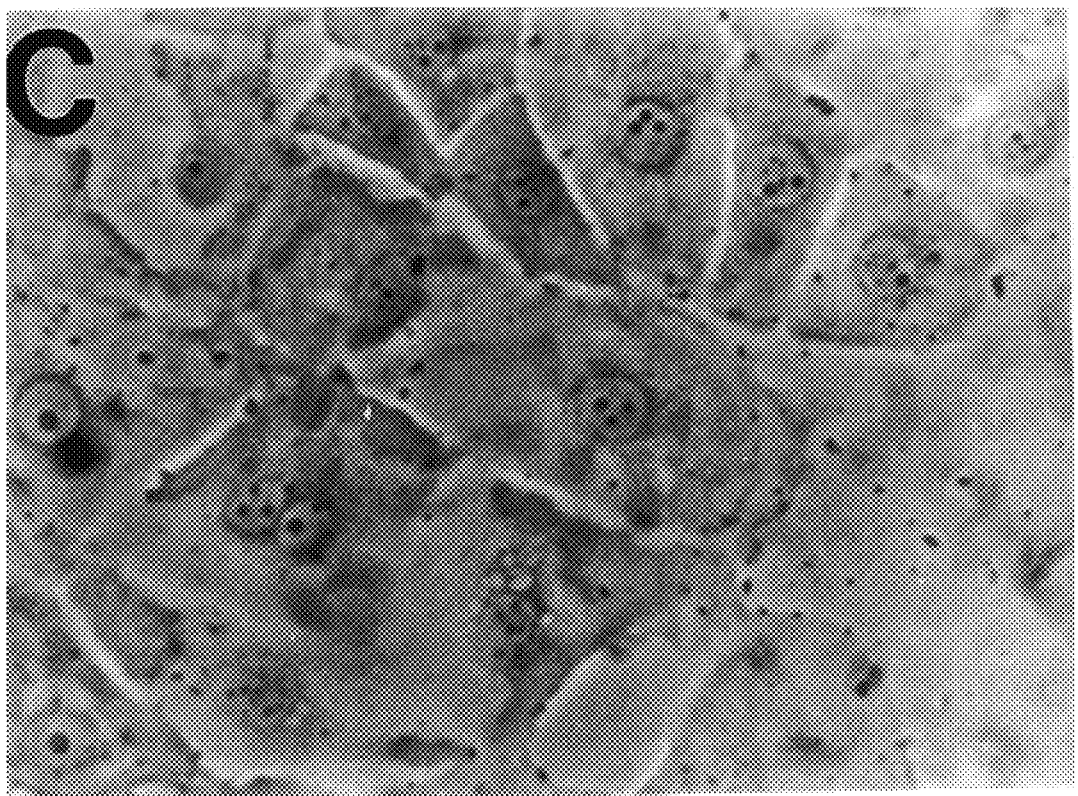

FIGS. 6A–6C. Effect of beclin transfection on the morphology of human MCF7 breast carcinoma cells.

6A. Western blot analysis of flag-Beclin expression in MVF7 clones transfected with BC252SV40/beclin. BHK cell lysates infected with a recombinant Sindbis virus expressing flag-tagged Beclin is used as a positive control (lane 1). MCF7 Beclin clones 1, 4 and 7 (lanes 2, 3 and 4 respectively) and a control MCF7 clone (lane 5).

6B. Phase contrast micrographs of MCF7 control clone 5 cells, and

6C. MCF7 Beclin clone 17 cells at 375×magnification.

Figure 7:
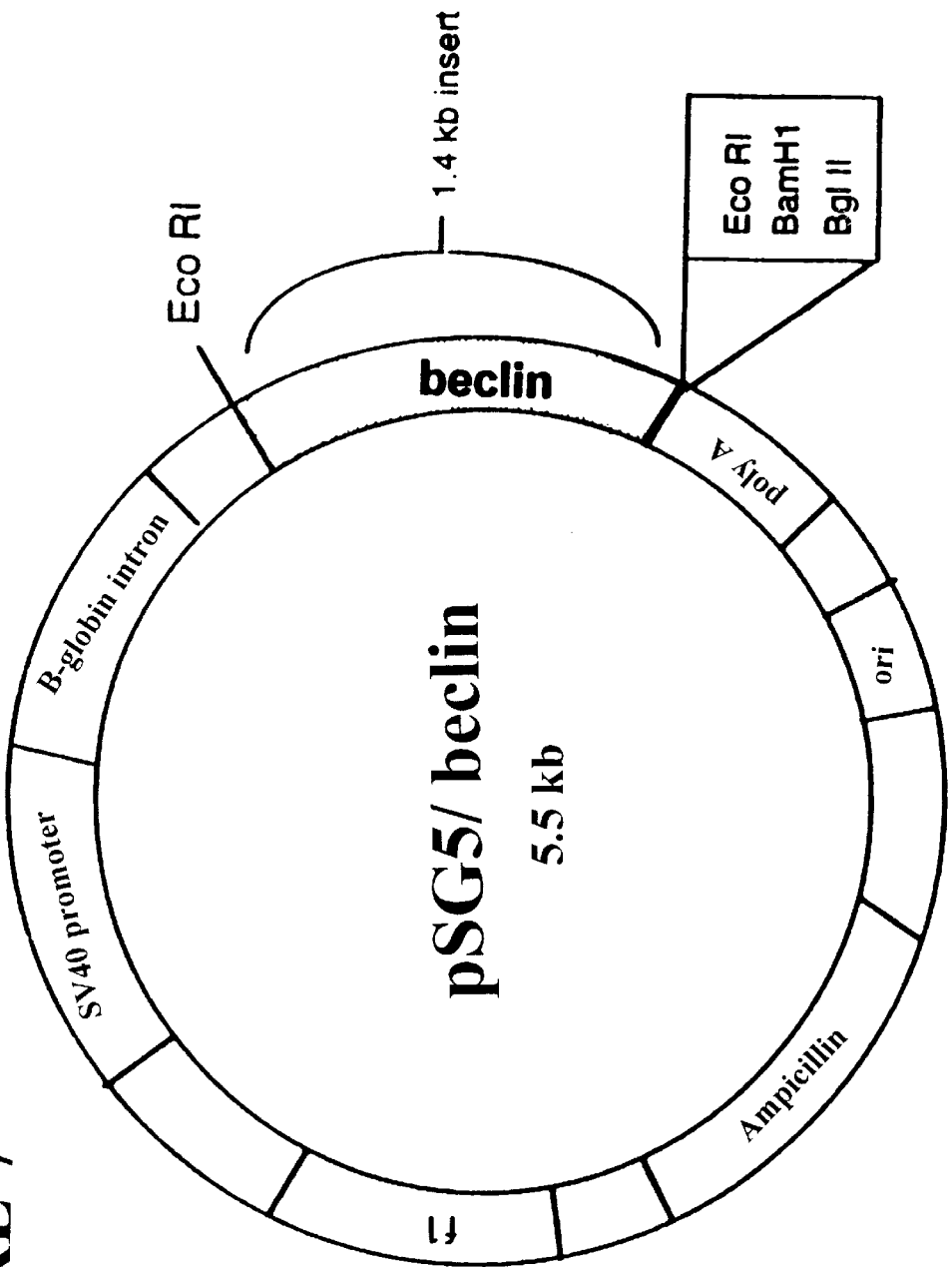

FIG. 7. Diagram of plasmid pSG5/beclin (ATCC Accession No. 97664). The 1.4 kb insert encoding Beclin was inserted into Eco RI sites in the plasmid, pSG5 (Stratagene).

DETAILED DESCRIPTION OF THE INVENTION

In order to facilitate an understanding of the Experimental Details section which follows, certain frequently occurring methods and/or terms are best described in Sambrook, et al.(1989).

Throughout this application, references to specific nucleotides are to nucleotides present on the coding strand of the nucleic acid. The following standard abbreviations are used throughout the specification to indicate specific nucleotides:

| C = cytosine | A = adenosine |
|---|---|
| T = thymidine | G = guanosine |

A "gene" means a nucleic acid molecule, the sequence of which includes all the information required for the normal regulated production of a particular protein, including the structural coding sequence, promoters and enhancers.

As used herein a wildtype human Beclin means a polypeptide which has an amino acid sequence identical to that present in a naturally-occurring form of human Beclin. As used here a mutant human Beclin means a polypeptide having an amino acid sequence which differs by one or more amino residues from any naturally occurring form, including deletions mutants containing less than all of the residues present in the wildtype polypeptide, substitution homologs wherein one or more residues are replaced by other residues, and addition homologs wherein on or more amino acid residues are added to a terminal or medial portion of the polypeptide.

The nucleic acids and oligonucleotides described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

The present invention provides for an isolated nucleic acid which encodes a wildtype human Beclin. This invention further provides an isolated nucleic acid which encodes a mutant human Beclin. The above-described isolated nucleic acids can be DNA, specifically cDNA or genomic DNA, and RNA. In a preferred embodiment, the wildtype Beclin has an amino acid sequence substantially identical to the amino acid sequence designated Seq. I.D. No.: 1. In another preferred embodiment, the isolated nucleic acid comprises a nucleic acid having a sequence substantially the same as the sequence designated Seq. I.D. No.: 2.

As used herein, "mutant human Beclin" means polypeptides that whose nucleic acid sequence or amino acid seqeunce differs from that of the naturally-occuring wildtype human Beclin. For example, due to a point mutation, the translated polypeptide differs from the naturally-occuring wildtype protein. Further, a subject may have low expression of the naturally-occurring protein so that the cells with this low-expressing protein cannot inhibit cell proliferation.

This invention also provides for a vector comprising the above-described nucleic acid operatively linked to a promoter of RNA transcription.

Numerous vector backbones are known in the art and are useful for expressing proteins. Such vectors include plasmid vectors, cosmid vectors, yeast artificial chromosome (YAC), bacteriophage or eukaryotic viral DNA. For example, one such class of vectors comprises DNA elements derived from viruses such as bovine papilloma virus, polyoma virus, adenovirus, vaccinia virus, baculovirus, retroviruses (RSV, MMTV or MoMLV), Semliki Forest virus or SV40 virus. Such vectors may be obtained commercially or assembled from the sequences described by methods well-known in the art.

This invention specifically provides a plasmid designated pSG5/beclin. Plasmid pSG5/beclin was made by cleaving DNA which encodes a wildtype human Beclin and inserting the DNA into the Eco RI site of pSG5 (FIG. 5). pSG5/beclin was deposited on Jul. 18, 1996 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. pSG5/beclin has been accorded ATCC Accession Number 97664.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk cells and COS cells. Mammalian cells may be transfected by methods well known in the art such as calcium phosphate precipitation, electroporation and microinjection.

This invention also provides a host vector system for the production of a polypeptide which comprises the above-described vector in a suitable host.

This invention also provides a method of producing a polypeptide which comprises growing the above-described host vector system, under suitable conditions permitting production of the polypeptide and recovering the polypeptide so produced. Further, this invention also provides a method of obtaining a polypeptide in purified form which comprises (a) introducing the above-described vector into a suitable host cell, (b) culturing the resulting host cell so as to produce the polypeptide, (c) recovering the polypeptide produced into step (b); and (d) purifying the polypeptide so recovered. In the above-described method, the vector comprises a plasmid, cosmid, yeast artificial chromosome (YAC), bacteriophage or eukaryotic viral DNA and the suitable host cell comprises a bacterial, insect, plant or mammalian cell.

This invention also provides a purified, wildtype human Beclin. Wildtype human Beclin means a polypeptide which has an amino acid sequence identical to that present in a naturally-occurring form of human Beclin.

This invention also provides an oligonucleotide of at least 15 nucleotides capable of specifically hybridizing with a unique sequence of nucleotides within a nucleic acid which encodes a wildtype Beclin without hybridizing to any sequence of nucleotides within a nucleic acid which encodes a mutant human Beclin. Further, this invention also provides an oligonucleotide of at least 15 nucleotides capable of specifically hybridizing with a unique sequence of nucleotides within a nucleic acid which encodes a mutant Beclin without hybridizing to any sequence of nucleotides within a nucleic acid which encodes a wildtype human Beclin. The above-described oligonucleotides may DNA or RNA. Methods of manufacturing such oligonucleotides and using the oligonucleotides are well-known in the art.

This invention also provides a method for determining whether a subject has a predisposition for cancer which comprises (a) obtaining an appropriate nucleic acid sample from the subject; and (b) determining whether the nucleic acid sample from step (a) is, or is derived from, a nucleic acid which encodes a mutant human Beclin so as to thereby determine whether a subject has a predisposition for cancer. Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the sequence designated Seq. I.D. No.: 2, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which as an amino acid sequence designated Seq. I.D. No.: 1 so as to thereby determine whether the nucleic acid sample is, or is derived from, a nucleic acid which encodes a mutant human Beclin.

In another example, the determining of step (b) comprises (i) amplifying the nucleic acid present in the sample of step (a); and (ii) detecting the presence of the mutant human Beclin in the resulting amplified nucleic acid.

The above-described methods of determining are well-known to those skilled in the art. In a preferred embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

Further, the cancer includes, but is not limited to, ovarian or breast cancers.

This invention also provides a method for determining whether a subject has cancer, which comprises (a) obtaining an appropriate nucleic acid sample from the subject; and (b) determining whether the nucleic acid sample from step (a) is, or is derived from, a nucleic acid which encodes a mutant human Beclin so as to thereby determine whether a subject has cancer.

Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the sequence designated Seq. I.D. No.: 2, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which as an amino acid sequence designated Seq. I.D. No.: 1 so as to thereby determine whether the nucleic acid sample is, or is derived from, a nucleic acid which encodes a mutant human Beclin.

In another example, the determining of step (b) comprises (i) amplifying the nucleic acid present in the sample of step (a), and (ii) detecting the presence of the mutant human Beclin in the resulting amplified nucleic acid.

The above-described methods of determining are well-known to those skilled in the art. In a preferred embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

Further, the cancer includes, but is not limited to, ovarian or breast cancers.

This invention also provides for a method for inhibiting cell proliferation in cells unable to regulate themselves by introducing the isolated nucleic acid which encodes a wildtype human Beclin into the cells, specifically wherein the cells are cancerous. Various methods of introducing nucleic acids into cells are well-known to those skilled in the art.

This invention also provides a method for treating a subject who has cancer which comprises introducing the isolated nucleic acid which encodes a wildtype human Beclin, into the subject so as to thereby treat the cancer. Various methods of introducing nucleic acids into cells are well-kwown to those skilled in the art.

In one example, one can introduce the isolated nucleic acid by (a) recovering cancer cells from the subject, (b) introducing the isolated nucleic acid of claim 1 into the cells; and (c) reintroducing the cells of step (b) into the subject so as to treat the subject who has cancer. Many types of cancer cells exist and are well-known in the art, specifically, breast, ovarian, skeletal, cervical, colon, prostate or lung cells.

This invention also provides a pharmaceutical composition comprising a purified wildtype human Beclin and a pharmaceutically acceptable carrier. This invention further provides a pharmaceutical composition comprising the polypeptide obtained from using the above-described method of obtaining a polypeptide in a purified form and a pharmaceutically acceptable carrier.

This invention also provides a method for treating a subject who has cancer comprising administration of an effective amount of the above-described pharmaceutical compositions to the subject who has cancer. The administration of the pharmaceutical compositions may be by topical, oral, aerosol, subcutaneous administration, infusion, intralesional, intramuscular, intraperitoneal, intratumoral, intratracheal, intravenous injection, or liposome-mediate delivery.

This invention also provides a method for detecting the presence of human chromosomal region 17q21 in a sample of genomic DNA which comprises (a) contacting the sample with the isolated nucleic acid which encodes a wildtype human Beclin, under conditions permitting formation of a complex between any genomic DNA present in the sample that is complementary to such nucleic acid, and (b) detecting the presence of any complex formed in step (a), the presence of such a complex indicating the human chromosomal region 17q21 is present in the sample.

Further, one may contacting the sample with an oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting formation of a complex between any genomic DNA present in the sample that is complementary to such oligonucleotide, and (b) detecting the presence of any complex formed in step (a), the presence of such a complex indicating the human chromosomal region 17q21 is present in the sample. The nucleic acid may be labeled with a detectable marker, wherein the detectable marker is a radioactive isotope, a fluophor or an enzyme.

This invention also provides a method for detecting a mutant human Beclin in a subject which comprises (a) obtaining an appropriate nucleic acid sample from the subject, and (b) determining whether the nucleic acid sample from step (a) is, or is derived from, a nucleic acid which encodes mutant human Beclin so as to thereby detect a mutant human Beclin in the subject.

Various methods of determining whether the nucleic acid sample is, or is derived from, a nucleic acid which encodes a mutant human Beclin exist.

In one example, the nucleic acid sample in step (a) comprises mRNA corresponding to the transcript of DNA encoding a mutant Beclin, and wherein the determining of step (b) comprises (i) contacting the mRNA with the above-described oligonucleotide, which is capable of specifically hybridizing with a unique sequence of nucleotides within a nucleic acid which encodes a mutant Beclin without hybridizing to any sequence of nucleotides within a nucleic acid which encodes a wildtype human Beclin, under conditions permitting binding of the mRNA to the oligonucleotide so as to form a complex, (ii) isolating the complex so formed, and (iii) identifying the mRNA in the isolated complex so as to thereby determine whether the mRNA is, or is derived from, a nucleic acid which encodes a mutant human Beclin.

In another example, the determining of step (b) comprises (i) contacting the nucleic acid sample of step (a), and the isolated nucleic acid which encodes a wildtype human Beclin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes a mutant human Beclin.

In another example, the determining of step (b) comprises (i) sequencing the nucleic acid sample of step (a); and (ii) comparing the nucleic acid sequence of step (i) with the above-described isolated nucleic acid having a sequence substantially the same as the sequence designated Seq. I.D. No,: 2, so as to thereby determine whether the nucleic acid sample is, or is derived from, a nucleic acid which encodes a mutant human Beclin.

In another example, the nucleic acid sample in step (a) comprises mRNA corresponding to the transcript of DNA encoding mutant Beclin, and wherein the determining of step (b) comprises (i) translating the mRNA under suitable conditions to obtain an amino acid sequence; and (ii) comparing the amino acid sequence of step (i) with the above-described isolated nucleic acid which as an amino acid sequence designated Seq. I.D. No.: 1 so as to thereby determine whether the nucleic acid sample is, or is derived from, a nucleic acid which encodes a mutant human Beclin.

In another example, the determining of step (b) comprises (i) amplifying the nucleic acid present in the sample of step (a); and (ii) detecting the presence of the mutant human Beclin in the resulting amplified nucleic acid.

The above-described methods of determining are well-known to those skilled in the art. In a preferred embodiment, the isolated nucleic acid or the oligonucleotide is labeled with a detectable marker, wherein the detectable marker is a radioactive isotope, a fluorophor or an enzyme.

Further, in a specific embodiment, the sample comprises blood, tissue or sera.

This invention also provides a method for treating a subject unable to control apoptosis in the cells of the subject which comprises introducing the isolated nucleic acid of claim 1, into the subject so as to treat the subject unable to control apoptosis in the cells of the subject. In a specific embodiment, the cells are cancerous. Various method of introducing isolated nucleic acids into cells exist and are well-known in the art. In one example, one can introduce the isolated nucleic acid by (a) recovering cancer cells from the subject, (b) introducing the isolated nucleic acid of claim 1 into the cells; and (c) reintroducing the cells of step (b) into the subject so as to treat the subject who has cancer.

This invention also provides a method of treating a subject unable to control apoptosis in the cells of the subject comprising administration of an effective amount of the above-described pharmaceutical compositions to the subject, wherein the administration comprises, topical, oral, aerosol, subcutaneous administration, infusion, intralesional, intramuscular, intraperitoneal, intratumoral, intratracheal, intravenous injection, or liposome-mediate delivery.

This invention is illustrated in the Experimental Details section which follows. These sections are set forth to aid in an understanding of the invention but are not intended to, and should not be construed to, limit in any way the invention as set forth in the claims which follow thereafter.

Experimental Details

Cell proliferation and apoptosis may share common pathways. Yet, in death repressor pathways, no direct links have been identified between cellular genes that inhibit apoptosis and cellular genes that inhibit proliferation. To investigate the mechanism by which anti-apoptotic genes function, the yeast two hybrid system was used to screen an adult mouse brain cDNA library for genes encoding proteins that interact with Bcl-2. Both Bcl-2 and its related family member, Bcl-$x_L$ interact with a novel 60 kd protein, Beclin, encoded by a gene on a specific region of chromosome 17q21 that is postulated to contain a tumor suppressor gene important in sporadic breast and ovarian cancer. Loss of function mutations in the conserved BH1 domains of Bcl-2 and Bcl-$x_L$ disrupt binding with Beclin, and antisense beclin blocks the ability of bcl-2 to protect cells Sindbis virus-induced apoptosis. Furthermore, beclin overexpression inhibits the proliferation of rat prostate adenocarcinoma AT3 cells and mouse NIH 3T3 fibroblast cells as well as the formation of human MCF7 breast tumor in nude mice. Together, these finds suggest that beclin is a novel bcl-2-interacting, candidate tumor suppressor gene that may link regulation of cellular proliferation with death repressor pathways.

The common deletion unit, located approximately 60 kb centromeric to BRCA1 that is postulated to contain an additional tumor suppressor gene important for ovarian and possibly breast cancer, contains 12 previously identified genes (Friedman, et al., 1995). Six of them are known genes or human homologs of other species, gamma tubulin, homolog of *D. melanogaster* enhancer of zeste, pseudogene of HMG17, homolog of Pacific electric ray VAT1, glucose-6phosphatase and Ki antigen. The remaining six genes are novel genes, one of which is the gene referred to as beclin that is described in this invention.

The mapping of beclin to this common deletion unit on chromosome 17q21, coupled with data that Beclin interacts with Bcl-2 and has anti-proliferative effects, raises the possibility that Beclin may function as a tumor suppressor gene important in ovarian and breast cancer.

EXAMPLE 1

Yeast Two Hybrid cDNA Library Screen To Isolate Bcl-2-interacting Proteins. To further understand the mechanism by which bcl-2 protects against apoptosis, the yeast two hybrid system was used to screen a mouse brain library for complementary cDNAs encoding proteins that bind to Bcl-2. A bait plasmid (pGBT9/bcl-2) was constructed by fusing human bcl-2 (lacking the C' terminal signal-anchor sequence to ensure translocation to the nucleus) to the GAL4 DNA-binding domain, which was cotransformed with an oligo (dT) and random hexamer primed adult mouse brain cDNA fusion library in a GAL4-activating domain vector, pGAD10. pGBT9/bcl-2 was co-transformed with 1×10$^6$ cDNAs from a mouse brain library fused to a GAL-4 activation domain vector (Clontech), plated onto SD medium lacking tryptophan and leucine, and after incubation at 30° C. for 4 days, screened for LacZ activity using a colony lift filter assay. Putative interacting clones were isolated by manipulation in leuB *E. Coli,* and further tested against pGBT9 and control plasmids. Of one million transformants, one true positive colony (F1) was identified by the X-Gal filter assay. A positive β-gal reaction between pGBT9/bcl-2 and clone F1 was obtained within 15–20 minutes. The sequence of the Eco RI insert in clone F1 was obtained using Sequenase and by automated dideoxy sequencing. Sequencing analysis of the cDNA plasmid rescued from this colony revealed a termination codon 42 base pairs downstream from the GAL 4 activation domain, several predicted short open reading frames between nucleotides 124 and 1843, and a longer predicted open reading frame spanning from nucleotide 1855 to 2500(the 3' end of the insert), suggesting that either the 14 amino acid fusion protein was interacting with Bcl-2, or one of the downstream open reading frames encoded a protein that contains its own activation domain and interacts with Bcl-2. To identify the Bcl-2-interacting region of F1, nucleotides 1–1854 and 1855–2500 were fused to the GAL4 activation domain in pGAD424 and tested for interactions with Bcl-2. Nucleotides 1855–2500, but not 1–1800, encoded a protein that specifically interacts with Bcl-2 (Table 1) but not with control GAL4 DNA binding domain plasmids containing p53, lamin (Table 1) or Sindbis virus glycoproteins.

A database search revealed that the sequence of F1:1855–2500 overlapped with several clones isolated from a normalized infant human brain cDNA library in the Merck EST database as well as clones from human breast (GT197) (Rommens, 1995) and human fibroblast cells (B32) (Friedman, 1994). Clones GT197 and B32 were both isolated in the generation of transcription maps of the breast cancer susceptibility locus on chromosome 17q21 and are mapped to a region located approximately 100 kilobases centromeric to the gene BRCA1. They lie within a 400 kb deletion unit mapped in sporadic ovarian cancers that contains 12 genes, including six genes with known function and six novel genes (Tangir, J., et al., 1996). This minimal deletion unit centromeric to BRCA1 is postulated to contain a tumor suppressor gene important for sporadic breast and ovarian cacner. These clones contain only partial open reading frames of a novel gene that encodes a protein with coiled coils. The gene was assigned the name beclin, because of the interaction of its encoded protein with bcl-2 (becl) and the predicted coiled coil structure of its encoded protein (in suffix).

The overlapping partial clones in Genbank were aligned with the mouse beclin sequence to obtain a predicted sequence of the full-length open reading frame for human beclin. Human beclin was isolated from a normalized human brain infant cDNA library (Soares, 1994). Human Beclin is homologous with the *C. elegans* T19E7.3 gene product (GENBANK accession U42843) and the *S. cerevisiae* gene product Lph7p (GENBANK accession U43503) (38% and 37% identical over 145 and 137 residues, respectively) indicating a high degree of evolutionary conservation.

TABLE 1

Summary of yeast two-hybrid assay results

| | GAL4 BD | | | | | | |
|---|---|---|---|---|---|---|---|
| GAL4 AD | Empty | Bcl-2 | Bcl-$X_L$ | Bcl-$X_S$ | Bax | Lamin | p53 |
| Empty | – | – | – | + | – | – | – |
| F1 | – | + | + | ND | – | – | – |
| F1: 1–1855 | – | – | – | ND | – | – | – |
| F1: 1856–2563 (Mus Beclin 1–708) | – | + | + | ND | – | – | – |
| Hu Beclin 1–708 | – | + | + | ND | – | – | – |
| Hu Beclin 1–450 | – | + | + | ND | – | – | – |
| Hu Beclin 1–258 | – | – | – | ND | – | – | – |
| Hu Beclin 262–450 | – | + | + | ND | – | – | – |
| Hu Beclin 451–708 | – | – | – | ND | – | – | – |
| Hu Beclin 1–1353 | – | – | – | ND | – | – | – |

The sequences encoding amino acids 1–218 of human bcl-2, 1–212 of bcl-$x_L$, 1–149 of bcl-$x_S$, and 1–171 of bax were cloned into pGBT9 in frame with the GAL4-binding domain. To avoid problems with targeting or proteins to the nucleus, the sequence encoding C' terminal transmembrane domains were omitted. To construct pGBT9/bcl-2, human bcl-2 was amplified by PCR from the plasmid pZIP/bcl-2, subcloned into pCR$^{TMII}$, and the correct sequence of bcl-2 was confirmed prior to cloning an EcoR I-Sal I fragment into pGBt9. To construct pGBT9/bcl-$x_L$, pGBT9/bcl-$x_S$, and pGBT9/bax, the EcoR I-Xho I fragment were excised from pGEG202 plasmids previously described and cloned into the Eco RI-Sal I sites of pGBT9. Control pB=GBT9 plasmids containing lamin (pLAM 5') and p53 (ppVA3) inserts were obtained from Clontech. pGBT9/bcl-2 was co-transformed with 1×10$^6$ cDNAs from a mouse brain library fused to a GAL-4 activation domain vector (Clontech), plated onto SD medium lacking tryptophan and leucine, and after incubation at 30° C. for 4 days, screened for LacZ activity using a colony lift filter assay. Putative interacting clones were isolated by manipulation in leuB *E. Coli*, and further tested against pGBT9 and control plasmids. A positive B-gal reaction between pGBT9/bcl-2 and clone F1 was obtained using Sequenase and by automated dideoxy sequencing. Additional clones containing fragments of F1 or human beclin fused to the GAL4-activation domain were constructed using PCR primers which incorporated Eco RI and Sal I restriction sites into the forward and reverse primers, respectively.

Additional yeast two hybrid studies were performed to confirm that human beclin, like mouse beclin, encodes a protein that interacts with human Bcl-2, and to further define the Bcl-2-interacting region of human Beclin (see Table 1). Additional clones containing fragments of F1 or human beclin fused to the GAL4-activiation domain were constructed using PCR primers which incorporated Eco Ri and Sal I restriction sites into the forward and reverse primers, respectively.

Sequencing Of Human Beclin. Primers immediately upstream and downstream of the predicted open reading frame were used to amplify the coding sequence of human beclin from a normalized human infant brain cDNA library (Soares, 1994). The resulting PCR products from several independent reactions were cloned into pCR$^{TMII}$ and sequenced in both directions using Sequenase (US Biochemicals) as well as automated sequencing. The resulting nucleotide sequence (FIG. 1B, Seq. I.D. No.: 2) and deduced amino acid sequence (FIG. 1A, Seq. I.D. No.: 1)

were used to scan various data banks (Genbank, EMBL, SwissProt, PIR) for homologous sequences using the BLAST algorithms (Altschul, 1990). The amino acid sequence was also analyzed by the PROSITE program to identify functional motifs and by the COILS program to identify coiled coil regions (Lupas, 1991).

Yeast Two Hybrid Analyses of Beclin-Bcl-2 Family Member Interactions. To investigate whether Beclin interacts with other Bcl-2 family members that positively or negatively regulate apoptosis, bax, bcl-$x_S$ and bcl-$x_L$ cDNAs were fused into the GAL4 binding domain vector and tested for interactions with Beclin in the yeast two hybrid system. (See Table 1).

The sequences encoding amino acids 1–218 of human bcl-2, 1–212 of bcl-$x_L$, 1–149 of bcl-$x_S$, and 1–171 of bax were cloned into pGBT9 in frame with the GAL4-binding domain. To avoid problems with targeting of proteins to the nucleus, the sequences encoding C'terminal transmembrane domains were omitted. To construct pGBT9/bcl-2, human bcl-2 was amplified by PCR from the plasmid pZIP/bcl-2, subcloned into pCR$^{TMII}$, and the correct sequence of bcl-2 was confirmed prior to cloning an Eco RI-Sal I fragment into pGBT9. To construct pGBT9/bcl-$x_L$, pGBT9/bcl-$x_S$, and pGBT6/Bax, the Eco RI-Xho I fragments were excised from pGEG202 plasmids previously described (Sato, et al., 1994) and cloned into the Eco RI-Sal I sites of pGBT9. Control pGBT9 plasmids containing lamin (pLAM5') and p53 (pVA3) inserts were obtained from Clontech.

The Bcl-$x_S$ GAL4 DB construct activated transcription by itself, and therefore could not be tested for interactions with Beclin. The same region of Beclin (aa 88–150) that interacted with Bcl-2, also interacted with Bcl-$x_L$ (Boise, 1993), a related Bcl-2 family member that inhibits apoptosis. In contrast, Beclin did not react with Bax (Oltvai, 1993), a family member that promotes apoptosis. The selective interaction of Beclin with Bcl-2 family members that have death repressor activity suggests a possible functional role of Beclin in anti-apoptotic pathways.

Full-length human Beclin does not interact with Bcl-2 in the yeast two-hybrid system. This most likely reflects lack of translocation to the nucleus in yeast secondary to association with yeast intracellular membranes since full-length human Beclin expressed in mammalian cells is associated with the insoluble membrane fraction after cell lysis.

To evaluate whether Bcl-2-Beclin and Bcl-$x_L$-Beclin interactions are related to the ability of Bcl-2 and Bcl-$x_L$ to inhibit apoptosis, pGBT9 vectors were constructed containing bcl-2 and bcl-$x_L$ constructs with mutations in the conserved BH1 domain that are known to block death repressor activity. A G→A mutation at amino acid position 145 of Bcl-2 completely abrogates Bcl-2 death-repressor activity in interleukin-3 deprivation, γ-irradiation and glucocorticoid-induced apoptosis (Yin, 1994), and also blocks Bcl-2 binding to beclin in the yeast two hybrid system (Table 2). Similarly, substitutions of amino acids 136–138 of Bcl-$x_L$ (VNW-->AIL) completely abolishes death repressor activity in Sindbis virus-induced apoptosis (Cheng, 1996), and also blocks Bcl-$x_L$ binding to Beclin. Thus, mutations that block anti-death activity of bcl-2 and bcl-$x_L$ also block binding to beclin.

TABLE 2

Effect of BH1 domain mutations on the ability of Bcl-2 and Bcl-$x_L$ to bind to beclin in the yeast two-hybrid assay

|   |   | Inhibition of Apoptosis | Beclin Binding |
|---|---|---|---|
| WT BCL-2 | ELFRDGVNWGRIVAFFEFGG | + | + |
| WT BCL-$X_L$ | ELFRDGVNWGRIVAFFSFGG | + | + |
| MT BCL-2 | ---------A---------- | − | − |
| MT BCL-$X_L$ | ------AIL----------- | − | − |

Oligonucleotide-directed mutagenesis of bcl-2 and bcl-$x_L$ was accomplished by a two-step polymerase chain reaction. Mutants were cloned into pCR$^{TMII}$ (In Vitrogen) and mutations were confirmed by dideoxy sequencing prior to cloning into pGBT9. PGBT9/bcl-2 and pGBT0/bcl-$x_L$ mutants were cotransformed with fragments of human beclin (1–450, 262–450, 1–708) fused to the GAL4-activation domain. Transformants were screened by B-galactosidase assays to determine whether mutations affected Beclin binding.

Analysis Of Beclin Expression In Mammalian Cells. Human beclin is predicted to encode a novel 450 amino acid protein, containing a coiled coil region with 25–28% homology with myosin-like proteins (FIG. 1A). Western blot analysis of lysates prepared from BHK cells infected with a Sindbis virus vector that expresses flag epitope-tagged Beclin confirms that human beclin encodes a 60 kd protein (FIG. 2A).

To construct the plasmid SIN/flag-beclin, human beclin was amplified by PCR from a human brain cDNA library, using primers that incorporated upstream and downstream Bst EII sites and an upstream sequence encoding the flag epitope. The Bst EII flag-beclin fragment was ligated into the Bst EII restriction site of the previously described double subgenomic SIN vector, ds633. Recombinant virus stocks were generated from SIN/flag-beclin plasmid as described. BHK cells were infected with SIN/flag-beclin or control constructs at a multiplicity of infection (MOI) of 1 plaque-forming unit per cell and harvested 15 hours after infection.

PROSITE analysis of human beclin identified several potential phosphorylation and myristoylation sites, but no other functional sequence motifs. RNA blot analysis revealed that expression of beclin mRNA is widespread in both mouse and human adult tissues. A beclin-specific probe hybridized to a 2.3 kb transcript present at highest levels in human skeletal muscle, but at detectable levels in all tissues examined (FIG. 2B). In some tissues, additional 1.7 and 1.4 kb transcripts were observed, suggesting the presence of alternately spliced transcripts.

To examine the subcellular localization of Beclin in mammalian cells and to determine whether Beclin colocalizes with Bcl-2, baby hamster kidney cells were transmitted with the plasmids, pSG5/bcl-2 and pSG5/beclin, that express Bcl-2 and a flag-epitope tagged Beclin, respectively. Immunofluorescence staining with an anti-flag epitope antibody and an anti-Bcl-2 antibody revealed that both proteins were expressed in the perinuclear membrane/endoplasmic reticulum region (FIG. 2C). Confocal laser microscopic analysis of BHK cells co-transfected with flag-epitope-tagged Beclin and Bcl-2 revealed that Beclin (FIG. 2C), like BCL-2 (FIG. 2D), displays a punctate pattern of immunoreactivity that is characteristic of association with intracellular organelles. Thus, Bcl-2 and Beclin colocalize in transfected mammalian cells.

Beclin's Ability To Interact With Bcl-2. When expressed in transient transfection assays, flag-tagged full-length human Beclin displays an punctate immunoreactivity pattern suggestive of association with intracellular organelles and is associated with the insoluble fraction after cell lysis. In contrast, a flag-tagged truncated Beclin (a.a. 1–236) (corresponding to the region isolated in the yeast two hybrid screen) displays a diffuse cytoplasmic staining pattern and is soluble after cell lysis (Liang and Levine, unpublished data). These differences between full-length and truncated Beclin are thought to account for differences in ability to translocate to yeast nuclei and interact with Bcl-2 in the yeast two hybrid assay.

The ability of human Beclin to bind to Bcl-2 in the yeast two-hybrid system maps to amino acids 88–150 (nucleotides 262–450). Interestingly, the coding sequence for this region of Beclin is deleted in some human infant brain cDNA clones in the Merck EST database, suggesting that Beclin exists in at least two forms-including one form that contains a Bcl-2 binding domain and one form that lacks a Bcl-2 binding domain.

To examine whether a full-length human Beclin interacts with Bcl-2 in mammalian cells, a fluorescence resonance energy transfer (FRET) studies of COS cells co-transfected with Bcl-2 and flag epitope-tagged Beclin was performed. Beclin is a coiled coiled protein that may be associated with the cytoskeleton and it partitions with the insoluble fraction following cell lysis. For this technical reason, biochemical analyses of in vivo interactions between Bcl-2 and Beclin are difficult to perform. FRET is a fluorescence technique which can be used as a spectroscopic ruler to study and quantify the interactions of cellular components with each other (Stryer, L., 1978; Wu, P. and Brand, L., 1994; Wang, S. F., et al., 1993; Selvin, P. R., 1995; Gadella, T. W., 1994). In FRET, a fluorophor (donor) in an excited state may transfer its excitation energy to a neighboring chromophor (acceptor) nonradiatively through dipole-dipole interactions. The efficiency of this process varies most importantly as the inverse of the sixth power of the distance separating the donor and acceptor chromophores, and in practice, requires the distance between the donor and the acceptor flurophores to be close (usually not exceeding 50 Angstroms). The dependent of the energy transfer efficiency on the donor-acceptor separation provides the basis for this utility of this phenomenon in the study of cell component interactions. FRET has been used by a number of investigators to examine interactions of cellular constitutents (reviewed in Stryer, L., 1978; Wu, P. and Brand, L., 1994; Wang, S. F., et al., 1993; Selvin, P. R., 1995; Gadella, T. W., 1994) such as endosomal fusion events, ligand-dependent growth factor receptor aggregations, interactions of viral and cellular proteins with regulatorsof apoptosis (Liang, X. H., et al., 1994; Mahajan, N., et al., 1996; Herman, B., et al., 1997), and interactions of cellular cytoskeletal components (Root, D., 1997).

FRET can be detected by exciting the labeled specimen with light of wavelenghts corresponding to the absorption spectrum of the donor and then detecting light emitted at the wavelengths corresponding to the emission spectrum of the acceptor. FRET manifests itself by both quenching of donor fluorescence in the presence of acceptor and in sensitized emission of acceptor fluorescence. FRET microscopy was performed as described herein. The donor (FITC) filter set consisted of excitation (ex)=450–490 nm; dichroic mirror (dm)=510 nm; emission (em)=515–555 nM. The acceptor (Rhodamine) filter set consisted of [ex=546 nm; dm=580 nm; long pass]. Images obtained with these two filter sets were used to directly quantify the intensities of each fluorophore. The FRET filter set consisted of [ex=450–490 nm; dm-580 nm; em=580 long pass]. The signal recorded from this filter set is the FRET signa and is from energy that has transferred from FITC to Rhodamine molecules. A background image containing no cells was taken with each filter set and subtracted from images with cells. A mapping program written in house was used to map fluorescent cells and to quantify the intensity within each cell. Quantitative analysis of these mapped images required solving three equations, one for each filter set, which accounted for the excitation and detection of both labels in all three filter sets as well as the concentrations of the donor and acceptor molecules and the probability of energy transfer. The measured quantities are expressed as follows in which the first letter (upper case) indicates the filter set(A=acceptor; F=FRET; D=donor) and the second letter (lower case) indicates the labels preset (a=acceptor alone; f=acceptor and donor; d=donor alone). A solution of the equations is E=1/[aconc(RK=1)] where aconc=(AdFf-FdAf)/[(AdFa/Aa)−Fd]; R=(DaFf/Fa-Df/[aconc ((Fa/Aa)−FdDa/DdAa)−Ff+FdDf/Dd]; and K is proportional to the product of the ratio of the quantum yield of the two labels and the ratio of the absolute detection efficiencies of the two labels.

Flag epiope-taged Beclin was labled with donor fluorophor (FITC) and Bcl-2 was labeled with acceptor fluorophor (Rhodamine) (FIGS. 3A–I). As a control, the endoplasmic reticulum $Ca^2+$-ATPases (SERCA) with donor (FITC) and Bcl-2 with acceptor (Rhodamine) were used. Quantitative analysis of microscopic images (following corrections for cross-talk between filter sets and donor and acceptor concentrations) showed significantly more energy transfer in experimental cells with labeled Beclin and Bcl-2 than in control cells with labeled SERCA and Bcl-2. (The quantitative measure of FRET used is a value, E, proportional to the probability of energy transfer betweem any donor molecue and any acceptor molecule). For the experimental cells, $E_{beclin-Bcl-2}$=0.00325±0.00153 (N=410) and for the control cells, $E_{SERCA-Bcl-2}$=0.00065±0.00043 (N=775) (p=<0.0001; t test). These data demonstrate that Beclin and Bcl-2 exhibited FRET, providing evidence of an interaction between these two proteins in mammalian cells.

Role Of Beclin In Virus-Induced Apoptosis. Overexpression of many Bcl-2 family members (Boise, 1993; Oltvai, 1993) or Bcl-2 interacting proteins (Farrow, Takayama) results in either the acceleration or inhibition of apoptosis. The Sindbis virus vector system was employed, which has been previously used to study the anti-apoptotic function of several Bcl-2 family members (Cheng, 1996), to evaluate the effects of beclin overexpression on virus-induced apoptosis. This system uses Sindbis virus both as an inducer of apoptosis and as a vector, and provides a means of rapidly testing the ability of candidate death-regulatory genes to suppress or accelerate virus-induced apoptosis (Cheng, E. H., et al., 1996); Levine, B., et al., 1996). Chimeric recombinant Sindbis viruses were constructed that contain human beclin or bcl-2 inserts in the sense and antisense orientations. Bcl-2 expressed from the recombinant Sindbis virus delayed death in BHK cells, as indicated by 50% cell viability compared to 0% with control viruses at 30 hours post-infection. However, neither Beclin nor antisense beclin expressed from recombinant viruses delayed or accelerated virus-induced death (FIG. 4A). While Bcl-2 overexpression results in a significant delay in SIN-induced cell death of BHK cells, neither antisense beclin RNA nor beclin overexpression delays or accelerates virus-induced death. Therefore, rather than acting as an independent regulator of apoptosis, beclin may be a functional component of a pathway that is mechanistically involved in the death repressor activity of Bcl-2.

Role of Beclin In Cellular Proliferation. To test this hypothesis, Beclin was tested to see if it plays a role in the ability of Bcl-2 to inhibit virus-induced apoptosis in mammalian cells. A bcl-2-transfected rat prostate adenocarcinoma cell line (AT3/bcl-2 cells) that is resistant to Sindbis virus-induced apoptosis (Levine, 1996) was infected with chimeric Sindbis viruses containing beclin in either the sense or antisense orientation.

To construct the plasmid SIN/flag-beclin, human beclin was amplified by PCR from a human brain cDNA library, using primers that incorporated upstream and downstream Bst EII sites and an upstream sequence encoding the flag epitope. The Bst EII flag-beclin fragment was ligated into the Bst EII restriction site of the previously described double subgenomic SIN vector, ds633, and recombinant virus stocks were generated from SIN/flag-beclin plasmid as described. The recombinant chimeric viruses SIN/antisense bcl-2 SIN/antisense beclin were constructed using identical methods. The construction of SIN/CAT has been described previously.

At 72 hours after infection, 77% of cells infected with SIN/beclin and 66% of cells infected with a control chimeric virus, SIN/CAT were still alive (FIG. 4B). In contrast, only 35% of cells infected with SIN/antisense beclin were still alive. The magnitude of this increase in cell death is similar to that seen after infection with a virus containing bcl-2 antisense RNA. The ability of antisense beclin, like antisense bcl-2, to partially inhibit bcl-2 protection against Sindbis virus-induced apoptosis demonstrates a functional role for Beclin in the death repressor activity of Bcl-2.

In the course of the above experiments, an apparent inhibition of cellular proliferation in both BHK cells and AT3/bcl-2 cells infected with SIN/beclin was observed. The number of AT3/bcl-2 cells 24 hours after infection with SIN/beclin was reduced by more than 50% as compared to the number of AT3/bcl-2 cells that were mock-infected or infected with SIN/CAT (FIG. 5A), whereas no significant differences were observed in AT3/bcl-2 cell viability among the three groups (FIG. 5B). A similar antiproliferative effect of beclin was observed in control AT3/neo cells, although these cells die quickly after infection with SIN/beclin and it is difficult to accurately quantitate cell proliferation in the face of rapid cell death.

To confirm these findings in AT3 cells using a different experimental system, mouse fibroblast NIH 3T3 cell lines that conditionally express beclin or antisense beclin, using tetracycline-repressible expression vector.

The vectors was made by amplifying a full length human beclin from a human brain cDNA library (Soares, M. B., 1994) using PCR primers which incorporated Nhe I resriction sites, and cloned into the Nhe I cloning sites of the conditional expression vector, BC252SV40 (provided by Axel Pollack, GSF-Institut fur Klinische Molekularbiologie). BC252SV40 consists of pHEBO, an EBV-derived promoter (TP1) in which the EBNA2 binding site was replaced by the tet07 element and an expression cassette for the tTA transactivator under the control of a CMV promoter, and a hygromycin selection marker. tTA binds to tet07 in the absence of tetracycline, but not in its presence, and induced the transcription of genes under control of tet07. The plasmids BC252SV40, BC252SV40/beclin, and BC252SV40/antisense beclin were transfected into NIH 3T3 cells using PFX6 (inVitrogen) according to the manufacturer's instructions, and stable transfectants were selected for with 300 μg/ml hygromycin and maintained in 1 μg/ml tetracycline. Antisense beclin-transfected clones were screed for inducible antisense flag-beclin mRNA expression by performing RT-PCR in the presence and absence of tetracycline, using a forward primer that hybridizes with the nucleotide sequence encoding the flag epitope tag and a reverse primer corresponding to nucleotides 746–765 of human beclin. Beclin-transfected clones were screened for inducible flag-beclin mRNA expression by RT-PCR and flag-Beclin protein expression by performing immunobot analysis with an anti-flag M2 antibody (20 μg/ml) using previously described methods (Liang, X. H., 1995).

A tetracycline-responsive NIH 3T3 clone stably transfected with antisense beclin and a control NIH 3T3 clone transfected with an empty vector were infected with recombinant chimeric Sindbis viruses that express either wild-type Bcl-2 (SIN/bcl-2) or Bcl-2 containing a stop codon near the 5' terminus (SIN/bcl-2 stop) (FIG. 4C). In the presence of tetracycline (when antisense beclin expression is suppressed), protection against virus-induced death was observed in both SIN/bcl-2 infected NIH/antisense beclin cells as well as in control cells. However, in the absence of tetracycline (when antisense beclin is expressed), no protection against Sindbis virus-induced death was conferred by bcl-2 in NIH 3T3/antisense beclin cells. Thus, similar to the observation in AT3 cells, antisense beclin expression also blocks the death repressor activity of bcl-2 in NIH 3T3 cells.

Cell proliferation of tetracycline-responsive NIH 3T3/beclin and NIH 3T3 antisense beclin clones and HIH 3T3 control transfectants in the presence or absence of tetracycline was measured (FIG. 5C). Tetracycline had no effect on the proliferation of control NIH 3T3 cells transfected with empty vector. In the presence of tetracycline, NIH 3T3/beclin cells and NIH 3T3/antisense beclin cells proliferated at the same rate as control transfectants. However, when tetracycline was removed from the culture medium, the rate of cell growth was significantly delayed in beclin-expressing cells and conversely, was accelerated in antisense beclin-expressing cells. These data demonstrate a role for beclin in the regulation of NIH 3T3 cell growth.

In view of genetic data suggesting that chromosome 17q21 contains a second tumor suppressor gene (in addition to BRCA1) important in sporadic breast and ovarian cancer (reviewed in Tangir, J., et al., 1996; Vogelstein, B., et al., 1994), the effect of beclin gene transfer on human MCF7 breast carcinoma cells was evaluated. Wild-type MCF7 cells (which are derived from a tumor containing 17q21 LOH) (Holt, J. T., et al., 1996) were transfected with the BC252SV40 expression vector containing wild-type beclin and hygromycin-resistant clones were selected. As expected after transfection with a gene that may negatively regulate cell growth, in several independent transfections, very few hygromycin-resistant colonies were obtained that grew beyond 10–20 cells and which could be tested for gene expression. Among five hygromycin-resistant colonies that could be expanded, four had flag-beclin message RNA detectable by RT-PCR but only one of these clones had detectable flag-Beclin expression by Western blot analysis (clone 17) (FIG. 6A). The tetracycline-regulatable expression vector, BC2525V40 previously described was used for MCF7 transfections with beclin. However, no tetracycline-responsive hygromycin resistant MCF7 Beclin clones were obtained; result are presented using MCF7 Beclin clone 17 which constitutively expresses flag-Beclin. This clone was chosen for further analysis.

Morphologic changes suggestive of a less transformed phenotype were observed in MCF7 cells that express Beclin. Whereas control cell were small, refractile, and often rounded (FIG. 6B), MCF7 Beclin cells were significantly larger, more flat in appearance and more firmly attached to the tissue culture plate (FIG. 6C). Control cells grew to a higher density (FIG. 6B), while cells that expressed Beclin were contact-inhibited and grew as a monolayer in culture (FIG. 6C).

Similar morphologic changes were observed in many MCF7 colonies obtained after transfection with BC2525V40/beclin which could nvever be expanded for analysis of gene expression and further investigations, but not in MCF7 colonies obtained after transfection with the empty BC2525V40 vector.

To further evaluate anchorage-independent growth, the ability of MCF7 Beclin 17 and MCF7 control 5 clones to form colonies in soft agar was examined (see Table 3). Whereas MCF7 Beclin 17 cells were unable to form colonies in soft agar, the number of colonies formed by MCF7 control 5 cells averaged over 1100 per $5 \times 10^4$ cells plated.

TABLE 3

Effect of beclin transfection on MCF7 colony formation in soft agar and tumorigenicity in nude mice. Soft agar assays were performed as described (Jiang, W., et al., 1993) and results are presented as the means ± s.e. number of colonies per $5 \times 10^4$ plated cells/well for six wells. For tumorigenicity assays, five week-old female CD1nu/nu mice (Charles River Laboratories) were implanted with 1.7 mg estrogen/60 day release pellets (innovative Research of America) and injected subcutaneously with $5 \times 10^6$ MCF7 tumor cells. Mice were monitored biweekly for the development of tumors and tumor size was measured in two dimensions (length [a] and width [b]). Tumor volume was calculated according to $V = ab^2/2$. Mice were necropsied after eight weeks, and mean tumor volumes and weights were determined for the subgroup of mice with tumors present upon necropsy.

| Clone | # colonies ± s.e | # mice w/tumors/# mice injected | mean tumor volume (mm³) ± s.e. | mean tumor weight (mg) ± s.e. |
|---|---|---|---|---|
| MCF7 Beclin 17 | 0 ± 0 | 2/14* | 92 ± 17** | 80 ± 0** |
| MCF7 control 5 | 1047 + 189 | 8/9 | 375 ± 135 | 360 ± 200 |
| MCF7 control 7 | ND | 6/8 | 641 ± 178 | 490 ± 200 |
| MCF7 control 9 | ND | 4/6 | 530 ± 100 | 490 ± 300 |

*p = 0.002 vs. MCF7 control clones; Chi-square analysis
**p = NS

The ability of Beclin to suppress clonigenicity in soft agar assays suggested that it may also suppress tumorigenicity in vivo. Therefore, the ability of MCF7 Beclin 17 and three control clones to form tumors in five week old female nude mice implanted with slow-release pellets was compared. After an eight-week observation period, 66–77% of mice injected with control clones developed autopsy-confirmed tumors, as compared with only 14% of mice injected with Beclin-expressing cells, demonstrating that Beclin expression significantly decreases the incidence of tumor formation. The tumors that did develop in mice injected with MCF7 Beclin 17 cells tended to have reduced tumor volume and weight compared to those in mice injected with control MCF7 clones, but these differences were not statistically significant. No difference were observed with respect to the rate of tumor growth or tumor histology.

In summary, the yeast two hybrid system was used to isolate a cDNA that encodes a predicted coiled coil protein, Beclin, that interacts with members of the Bcl-2 family that negatively regulate apoptosis. A functional role for Beclin in anti-apoptotic pathways is suggested both by Bcl-2 and Bcl-$x_L$ mutational studies showing a correlation between disruption of anti-apoptotic function and binding to Beclin, and by studies in which beclin antisense RNA partially blocks Bcl-2-mediated protection against virus-induced apoptosis. While the function of beclin, when expressed at normal levels in mammalian cells, is still unknown, its overexpression can inhibit cellular proliferation. These observations are consistent with the hypothesis that Bcl-2 may inhibit apoptosis by interacting with a gene product that exerts effects on cellular proliferative machinery. Furthermore, these findings, coupled with previous studies that have mapped beclin transcripts to a breast and ovarian cancer susceptibility locus on chromosome 17q21 (Rommens, 1995; Friedman, 1994; Friedman, 1995), warrant additional investigation to determine whether beclin, and its interactions with Bcl-2, play a role in human cancer.

REFERENCES

Altschul, S. F., et al. (1990) *J. Mol. Biol.* 215: 403–410;
Boehme, S. A. and Lenardo, M. J. (1993) *Eur. J. Immunol* 23: 1552–1560;
Boise, L. H., et al. (1993) *Cell* 74: 597–608;
Borner, C. (1996) *J. Biol. Chem.* 271: 12695–12698;
Boyd, J., et al. (1994) *Cell* 79: 341–351;
Buttyan, R. (1991) "Genetic response of prostate cells to androgen deprivation: insights into the cellular mechanisms of apoptosis." In Tomei LD, Cope FO (eds): *Apoptosis: The Molecular Basis of Cell Death.* Plainview, N.Y.: Cold Spring Harbor Laboratory Press 157–173;
Cheng, E. H., et al. (1996) *Nature* 379: 554–556.
Chittenden, T. (1995) *Nature* 374: 733–736;
Clarke, A., et al. (1992) *Nature* 359: 328–330
Cropp, C. S, et al. (1993) *Cancer Res.* 53: 3382–3385;
Eccles, D. M., et al. (1992) *Oncogene* 7: 2069–2072;
Evan, G. I., et al. (1995) *Curr. Opin. Cell Biol.* 7: 825–834;
Evan, G. I., et al. (1996) *Cell* 69: 119–128;
Evan, G. I., et al. (1995) *Curr. Opin. Cell Biol.* 7: 825–834;
Farinelli, S. E. and L. A. Greene (1996) *J. Neurosci.* 16: 1150–1162;
Farrow, S. N., et al. (1995) *Nature* 374: 731–733;
Fernandez-Sarabia, M. J., et al. (1993) *Nature* 366: 274–275;
Freeman, R. S., et al. (1994) *Neuron* 12: 343–355;
Friedman, L. S., et al. (1994) *Cancer Res.* 54: 6374–6382;
Friedman, L. S., et al. (1995) *Genomics* 25: 256–263;
Futreal, P. A., et al. (1994) *Science* 266: 120–122;
Futreal, P. A., et al. *Cancer Res.* 52: 2624–2627;
Gadella, T. J., et al. (1994) *Biophys Chem.* 48: 221.
Hall, J. M., et al. (1990) *Science* 250: 1684–1689;
Hanada, M., et al. (1995) *J. Biol. Chem.* 270: 11962–11969;
Herman, B., et al. (1997) *J. Fluorescence* 7: 85.
Hockenbery, D., et al. (1993) *Cell.* 75:241–251;
Hosking, L., et al. (1995) *Nature Genet* 9: 343–344;
Jacks, T., et al. (1992) *Nature* 359: 295–300;
Jiang, W., et al. (1993) *Oncogene* 8: 3447.
Kane, D. J., et al. (1993) *Science.* 262:1274–1276.
Kiefer, M. C., et al. (1995) *Nature* 374: 736–739;
King, K. L. and Cidlowski, J. A. (1995) *J. Cell. Biochem.* 58: 175–180;
Lam, M. et al. (1994) *Proc Natl Acad Sci USA* 91:6569–6573.
Lee, E-H, et al. (1992) *Nature* 359: 288–294;
Levine, B. et al. (1996) *Proc. Natl. Acad. Sci USA* 93: 4810.

Levine, B., et al. (1993) *Nature* 361: 739–742;
Liang, X. H., et al. (1994) *Oncogene* 8: 2645.
Liang, X. H., et al. (1995) *J. Cell Biochem.* 57: 509.
Linette, G. P., et al. (1996) *Proc. Acad. Sci USA* 93: 9545.
Lupas, A., et al. (1991) *Science* 252: 1162–1164;
Mahajan, N., et al. (1996) *Mol. Cell Biol.* 7s: 347a.
Matzel, S., et al. (1996) *J. Exp. Med.* 183: 2219–2226;
Meikrantz, W. and Schlegel, R. (1996) *J. Biol. Chem.* 271: 10205.
Merajver, S. D., et al. (1995) *Nature Genet.* 9: 439–443;
Miki, Y., et al. (1994) *Science* 266: 66–71;
Miura, M., et al. (1993) *Cell* 75:653–660;
Oltvai, Z., et al. (1993) *Cell* 74: 609–619;
O'Reilly, L. A., et al. (1996) *EMBO J.* 24: 6979.
Park, J. R., and Hockenberry, D. M. (1996) *J. Cell. Biochem.* 60: 12–17;
Qin, X., et al. (1994) *Proc Natl Acad Sci USA* 91: 10918–10922;
Reed, J. C., et al. (1990) *J. Cell. Biochem.* 60: 23–32;
Rommens, J. M., et al. (1995) *Genomics* 28: 530–542;
Root, D. (1997) *Proc. Natl. Acad. Sci USA* 94: 5685.
Russell, S. E. H., et al. (1990) *Oncogene* 5: 1581–1583;
Saito, H., et al. (1993) *Cancer Res.* 53: 3382–3385;
Sambrook, et al. (1989) Molecular Cloning-A Laboratory Manual, 2nd Edition, Cold Spring Harbor Laboratory Press.
Sato, T., et al. (1994) *Proc. Natl. Acad. Sci USA* 91: 9238–9242;
Sedlak, T. W., et al. (1995) *Proc. Natl. Acad. Sci. USA* 92: 7834–7838;
Selvin, P. R. (1995) *Methods in Enzymol* 246: 400.
Shan, B. and Lee, W. H. (1994) *Mol Cell Biol* 14: 8166–8173;
Shi, L., et al. (1994) *Science* 263: 1143–1145;
Shibasaki, F., et al. (1997) *Nature* 386: 728.
Soares, M. B., et. al. (1994) *Proc. Natl. Acad. Sci USA* 91: 9228–9232;
Stryer, L. (1978) *Annu Rev. Biochem.* 47: 819.
Szabo, C. I. and King, M. C. (1996) *Hum. Mol. Genet.* 4 review: 1811–1817;
Takayama, S., et al. (1995) *Cell* 80: 279–284;
Takhashi, H., et al. (1995) *Cancer Res.* 55: 2998–3002;
Tanaka, N., et al. (1994) *Cell* 77: 829–839;
Tangir, J., et al. (1996) *Oncogene* 12: 735–740;
Tsujimoto, Y., et al. (1985) *Science* 228: 1440–1443;
Vairo, B., et al. (1996) *Oncogene* 13: 1511.
Wang, X. F., et al. (1993) *Bioimaging* 1: 30.
Wang, H-G., et al. (1994) *Oncogene* 90: 2751–2756.
White, E., et al. (1991) *J. Virol.* 65: 2968–2978;
Wu, P. and Brand, L. (1994) *Anal. Biochem.* 218: 1.
Wu, X., and Levine, A. J. (1994) *Proc Natl Acad Sci USA* 91: 3602–3606;
Wyllie, A. H., et al. (1987) *J. Cancer* 56: 251–259;
Yan-Feng, et al. (1993) *Int.J.Cancer* 54: 546–551;
Yang, E., et al. (1995) *Cell* 80: 285–291;
Yin, X. M., et al. (1994) *Nature* 369: 321–323.

What is claimed is:

1. An isolated nucleic acid which encodes a wildtype human beclin which comprises the amino acid sequence shown in SEQ ID NO: 1.

2. An isolated nucleic acid of claim 1, wherein the nucleic acis is DNA.

3. An isolated nucleic acid of claim 1, wherein the nucleic acid is RNA.

4. The isolated nucleic acid of claim 2, wherein the nucleic acid is cDNA.

5. The isolated nucleic acid of claim 1, wherein the nucleic acid comprises the nucleic acid sequence as set forth in SEQ ID NO:2.

6. A vector comprising the nucleic acid of claim 1 operatively linked to a promoter of RNA transcription.

7. The vector of claim 6, wherein the promoter is a bacterial, yeast, insect or mammalian promoter.

8. The vector of claim 7, further comprising plasmid, cosmid, yeast artificial chromosome (YAC), bacteriophage or eukaryotic viral DNA.

9. The plasmid of claim 8 designated pSG5/beclin (ATCC Accession Number 97664).

10. A host vector system for the production of a polypeptide which comprises the vector of claim 6 in a suitable host.

11. The host vector system of claim 10, wherein the suitable host comprises a prokaryotic or eukaryotic cell.

12. The host vector system of claim 11, wherein the prokaryotic cell is a bacterial cell.

13. The host vector system of claim 11, wherein the eukaryotic cell is a yeast, insect, plant or mammalian cell.

14. A method of producing a polypeptide which comprises growing the host vector system of claim 10 under conditions permitting the production of the polypeptide, and recovering the polypeptide so produced.

15. A method of obtaining a polypeptide in purified form which comprises:

(a) introducing the vector of claim 6 into a suitable host cell;
   (b) culturing the resulting host cell so as to produce the polypeptide;

(c) recovering the polypeptide produced in step (b); and (d) purifying the polypeptide so recovered.

16. The method of claim 15, wherein the vector comprises plasmid, cosmid, yeast artificial chromosome (YAC), bacteriophage or eukaryotic viral DNA.

17. The method of claim 15, wherein the suitable host cell comprises a bacterial, insect, plant or mammalian cell.

18. A purified, wildtype human Beclin comprising the amino acid sequence shown in SEO ID NO: 1.

19. An oligouncleotide which (a) consists of at least 15 nucleotide residues whose sequence is complementary to a coding portion of a nucleic acid that encodes a human Beclin whose amino acid sequence comprises that shown in SEQ ID NO:1, and (b) hybridizes to a nucleic acid encoding said Beclin without hybridizing to a nucleic acid encoding a protein whose amino acid sequence does not comprise that shown in SEQ ID NO:1.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 450 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
                20                  25                  30

Ile Leu Asp Arg Val Thr Ile Gln Glu Leu Thr Ala Pro Leu Leu Arg
            35                  40                  45

Arg Ala Gln Ala Lys Pro Gly Glu Thr Gln Glu Glu Thr Asn Ser
        50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
                85                  90                  95

Phe Thr Leu Ile Gly Glu Ala Ser Asp Gly Gly Thr Met Glu Asn Leu

```
                    100                 105                 110
Ser Arg Leu Lys Val Thr Gly Asp Leu Phe Asp Ile Met Ser Gly Gln
            115                 120                 125

Thr Asp Val Asp His Pro Leu Cys Glu Glu Cys Thr Asp Thr Leu Leu
    130                 135                 140

Asp Gln Leu Asp Thr Gln Leu Asn Val Thr Glu Asn Glu Cys Gln Asn
145                 150                 155                 160

Tyr Lys Arg Cys Leu Glu Ile Leu Glu Gln Met Asn Glu Asp Asp Ser
                165                 170                 175

Glu Gln Leu Gln Met Glu Leu Lys Glu Leu Ala Leu Glu Glu Glu Arg
            180                 185                 190

Leu Ile Gln Glu Leu Glu Asp Val Glu Lys Asn Arg Lys Ile Val Ala
        195                 200                 205

Glu Asn Leu Glu Lys Val Gln Ala Glu Ala Glu Arg Leu Asp Gln Glu
    210                 215                 220

Glu Ala Gln Tyr Gln Arg Glu Tyr Ser Glu Phe Lys Arg Gln Gln Leu
225                 230                 235                 240

Glu Leu Asp Asp Glu Leu Lys Ser Val Glu Asn Gln Met Arg Tyr Ala
                245                 250                 255

Gln Thr Gln Leu Asp Lys Leu Lys Lys Thr Asn Val Phe Asn Ala Thr
            260                 265                 270

Phe His Ile Gln His Ser Gly Gln Phe Gly Thr Ile Asn Asn Phe Arg
        275                 280                 285

Leu Gly Arg Leu Pro Ser Val Pro Val Glu Trp Asn Glu Ile Asn Ala
    290                 295                 300

Ala Trp Gly Gln Thr Val Leu Leu His Ala Leu Ala Asn Lys Met
305                 310                 315                 320

Gly Leu Lys Phe Gln Arg Tyr Arg Leu Val Pro Tyr Gly Asn His Ser
                325                 330                 335

Tyr Leu Glu Ser Leu Thr Asp Lys Ser Lys Glu Leu Pro Leu Tyr Cys
            340                 345                 350

Ser Gly Gly Leu Arg Phe Phe Trp Asp Asn Lys Phe Asp His Ala Met
        355                 360                 365

Val Ala Phe Leu Asp Cys Val Gln Gln Phe Lys Glu Glu Val Glu Lys
    370                 375                 380

Gly Glu Thr Arg Phe Cys Leu Pro Tyr Arg Met Asn Asp Val Glu Lys
385                 390                 395                 400

Gly Lys Ile Glu Asp Thr Gly Ser Gly Ser Tyr Ser Ile Lys
                405                 410                 415

Thr Gln Phe Asn Ser Glu Glu Gln Trp Thr Lys Ala Leu Lys Phe Met
            420                 425                 430

Leu Thr Asn Leu Lys Trp Gly Leu Ala Trp Val Ser Ser Gln Phe Tyr
        435                 440                 445

Asn Lys
    450

(2) INFORMATION FOR SEQ ID NO:2:

(i) SEQUENCE CHARACTERISTICS:
        (A) LENGTH: 1353 base pairs
        (B) TYPE: nucleic acid
        (C) STRANDEDNESS: single
        (D) TOPOLOGY: linear (iii) HYPOTHETICAL: NO
```

(iv) ANTI-SENSE: NO (xi) SEQUENCE DESCRIPTION: SEQ ID NO:2:

| | | | | | |
|---|---|---|---|---|---|
| ATGGAAGGGT | CTAAGACGTC | CAACAACAGC | ACCATGCAGG | TGAGCTTCGT | GTGCCAGCGC | 60 |
| TGCAGCCAGC | CCCTGAAACT | GGACACGAGT | TTCAAGATCC | TGGACCGTGT | CACCATCCAG | 120 |
| GAACTCACAG | CTCCATTACT | TACCACAGCC | CAGGCGAAAC | CAGGAGAGAC | CCAGGAGGAA | 180 |
| GAGACTAACT | CAGGAGAGGA | GCCATTTATT | GAAACTCCTC | GCCAGGATGG | TGTCTCTCGC | 240 |
| AGATTCATCC | CCCCAGCCAG | GATGATGTCC | ACAGAAAGTG | CCAACAGCTT | CACTCTGATT | 300 |
| GGGGAGGTAT | CTGATGGCGG | CACCATGGAG | AACCTCAGCC | GAAGACTGAA | GGTCACTGGG | 360 |
| GACCTTTTTG | ACATCATGTC | GGGCCAGACA | GATGTGGATC | ACCCACTCTG | TGAGGAATGC | 420 |
| ACAGATACTC | TTTTAGACCA | GCTGGACACT | CAGCTCAACG | TCACTGAAAA | TGAGTGTCAG | 480 |
| AACTACAAAC | GCTGTTTGGA | GATCTTAGAG | CAAATGAATG | AGGATGACAG | TGAACAGTTA | 540 |
| CAGATGGAGC | TAAAGGAGCT | GGCACTAGAG | GAGGAGAGGC | TGATCCAGGA | GCTGGAAGAC | 600 |
| GTGGAAAAGA | ACCGCAAGAT | AGTGGCAGAA | AATCTCGAGA | AGGTCCAGGC | TGAGGCTGAG | 660 |
| AGACTGGATC | AGGAGGAAGC | TCAGTATCAG | AGAGAATACA | GTGAATTTAA | ACGACAGCAG | 720 |
| CTGGAGCTGG | ATGATGAGCT | GAAGAGTGTT | GAAAACCAGA | TGCGTTATGC | CCAGACGCAG | 780 |
| CTGGATAAGC | TGAAGAAAAC | CAACGTCTTT | AATGCAACCT | TCCACATCTG | GCACAGTGGA | 840 |
| CAGTTTGGCA | CAATCAATAA | CTTCAGGCTG | GGTCGCCTGC | CCAGTGTTCC | CGTGGAATGG | 900 |
| AATGAGATTA | ATGCTGCTTG | GGGCCAGACT | GTGTTGCTGC | TCCATGCTCT | GGCCAATAAG | 960 |
| ATGGGTCTGA | AATTTCAGAG | ATACCGACTT | GTTCCTTACG | GAAACCATTC | ATATCTGGAG | 1020 |
| TCTCTGACAG | ACAAATCTAA | GGAGCTGCCG | TTATACTGTT | CTGGGGGGTT | GCGGTTTTTC | 1080 |
| TGGGACAACA | AGTTTGACCA | TGCAATGGTG | GCTTTCCTGG | ACTGTGTGCA | GCAGTTCAAA | 1140 |
| GAAGAGGTTG | AGAAAGGCGA | GACACGTTTT | TGTCTTCCCT | ACAGGATGGA | TGTGGAGAAA | 1200 |
| GGCAAGATTG | AAGACACAGG | AGGCAGTGGC | GGCTCCTATT | CCATCAAAAC | CCAGTTTAAC | 1260 |
| TCTGAGGAGC | AGTGGACAAA | AGCTCTCAAG | TTCATGCTGA | CGAATCTTAA | GTGGGGTCTT | 1320 |
| GCTTGGGTGT | CCTCACAATT | TTATAACAAA | TGA | | | 1353 |

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:3:

Glu Leu Phe Arg Asp Gly Val Asn Trp Gly Arg Ile Val Ala Phe Phe
1               5                   10                  15

Glu Phe Gly Gly
            20

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear -continued (iii) HYPOTHETICAL: NO (iv) ANTI-SENSE: NO (xi) SEQUENCE DESCRIPTION: SEQ ID NO:4:

Glu Leu Phe Arg Asp Gly Val Asn Trp Gly Arg Ile Val Ala Phe Phe
1               5                   10                  15

Ser Phe Gly Gly
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:5:

Glu Leu Phe Arg Asp Gly Val Asn Trp Ala Arg Ile Val Ala Phe Phe
1               5                   10                  15

Glu Phe Gly Gly
            20

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:6:

Glu Leu Phe Arg Asp Gly Ala Ile Leu Gly Arg Ile Val Ala Phe Phe
1               5                   10                  15

Ser Phe Gly Gly
            20